United States Patent
Baute et al.

(10) Patent No.: US 12,002,546 B2
(45) Date of Patent: *Jun. 4, 2024

(54) METHODS OF DETERMINING SENSITIVITY TO PHOTOPERIOD IN CANNABIS

(71) Applicant: Aurora Cannabis Enterprises Inc.

(72) Inventors: Gregory Baute, Comox (CA); Shumin Wang, Vancouver (CA); Jason Sawler, Centreville (CA); Jose Celedon, Vancouver (CA)

(73) Assignee: Aurora Cannabis Enterprises Inc., Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/720,128

(22) Filed: Apr. 13, 2022

(65) Prior Publication Data

US 2022/0235425 A1    Jul. 28, 2022

Related U.S. Application Data

(63) Continuation of application No. 17/439,757, filed as application No. PCT/CA2021/050442 on Mar. 31, 2021.

(30) Foreign Application Priority Data

Apr. 1, 2020   (CA) ..................... 3077823

(51) Int. Cl.
| | |
|---|---|
| G16B 20/20 | (2019.01) |
| A01H 1/00 | (2006.01) |
| A01H 6/28 | (2018.01) |
| G16B 20/00 | (2019.01) |
| G16B 20/40 | (2019.01) |

(52) U.S. Cl.
CPC .......... *G16B 20/20* (2019.02); *A01H 1/1215* (2021.01); *A01H 6/28* (2018.05); *C12Q 2600/13* (2013.01); *C12Q 2600/156* (2013.01); *G16B 20/00* (2019.02); *G16B 20/40* (2019.02)

(58) Field of Classification Search
CPC ........ G16B 20/20; G16B 20/00; G16B 20/40; A01H 1/1215; A01H 6/28
See application file for complete search history.

(56) References Cited

U.S. PATENT DOCUMENTS

2016/0177404 A1    6/2016   McKernan
2019/0082612 A1    3/2019   Bitetti

FOREIGN PATENT DOCUMENTS

| WO | 2021097496 A2 | 5/2021 | |
|---|---|---|---|
| WO | WO 2021/097496 A2 * | 5/2021 | ........... A01H 1/1215 |
| WO | WO 2022/035691 A1 | 2/2022 | |

OTHER PUBLICATIONS

Dai, Y., Li, W. and An, L., 2016. NMD mechanism and the functions of Upf proteins in plant. Plant cell reports, 35(1), pp. 5-15 (Year: 2016).*
Diaz et al., 2012. Copy number variation affecting the Photoperiod-B1 and Vernalization-A1 genes is associated with altered flowering time in wheat (Triticum aestivum). PloS one, 7(3), e33234 pp. 1-11. (Year: 2012).*
Mallikarjuna, B.P., 2015. Molecular mapping of flowering time genes in chickpea (*Cicer arietinum* L.) (Doctoral dissertation, University of Agricultural Sciences, Raichur-584104). (Year: 2015).*
Panerio, R.J.G., 2020. Hedging your bets: the importance of flowering time and agronomic practise in the search for the ideal Australian hemp seed cultivar (Doctoral dissertation, Southern Cross University). (Year: 2020).*
Pedró, J.P., 2020. Novel molecular tools to uncover the genetic architecture of hemp fibre quality (Doctoral dissertation, Wageningen University and Research). (Year: 2020).*
Salentijn et al., 2015. New developments in fiber hemp (*Cannabis sativa* L.) breeding. Industrial crops and products, 68, pp. 32-41. (Year: 2015).*
Shi et al., 2012. *Arabidopsis* plants having defects in nonsense-mediated mRNA decay factors UPF1, UPF2, and UPF3 show photoperiod-dependent phenotypes in development and stress responses. Journal of integrative plant biology, 54(2), pp. 99-114. (Year: 2012).*
Thomas, B., 2006. Light signals and flowering. Journal of experimental botany, 57(13), pp. 3387-3393. (Year: 2006).*
Zhu, C., 2016. High throughput approaches to study molecular pathways from genotype to phenotype (Doctoral dissertation, ETH Zurich) pp. 1-111. (Year: 2016).*
Michaels, S.D. and Amasino, R.M., 2001. Loss of Flowering Locus C activity eliminates the late-flowering phenotype of Frigida and autonomous pathway mutations but not responsiveness to vernalization. The Plant Cell, 13(4), pp. 935-941. (Year: 2001).*
International Search Report & Written Opinion of the International Searching Authority, dated Jul. 5, 2021, issued in International Application No. PCT/CA2021/050442, filed Mar. 31, 2021, 13 pages.

* cited by examiner

*Primary Examiner* — David H Kruse
(74) *Attorney, Agent, or Firm* — Christensen O'Connor Johnson Kindness PLLC

(57) ABSTRACT

This disclosure pertains to markers and methods useful in identifying *Cannabis* plants that have a day length neutral phenotype, and methods of breeding plants having a day length neutral phenotype.

9 Claims, No Drawings
Specification includes a Sequence Listing.

SEQUENCE LISTING

<160> NUMBER OF SEQ ID NOS: 54

<210> SEQ ID NO 1
<211> LENGTH: 6030
<212> TYPE: DNA
<213> ORGANISM: Cannabis sativa

<400> SEQUENCE: 1

```
gaattcccac aggaatgctt tctattaatc accaaagaat tactgaaaat agctcttcga      60
gaggctttct ctcctattct aacctttcaa gaaggctaga tctctcccaa gagatttctc     120
aattctaaac ccttttcaaca taactaaaac tgagttctga ttccctatgc atacacgata    180
gagaataaag cttcttcat agcaacttaa ttaaaagcta ctagccaata caaaaagaac      240
aattcagctt agaacaatta gaacaaagac taaaactgaa taaactgctg tcataaaact     300
tatgcttggc atttgtggct tttcctcttt cggtagacac atcaagggtt tatcaatatc     360
cctactaaaa tcttaccttg tcctcaagtg gaaatcatgc attgatagtt gagcaagtct     420
cctgtgtagc ttcaaagtca ggtagggagt gccattccat caaaacgttg gaatttgctt    480
gagtaccagc tgttataaaa tggtgttgga ggacctgtcc gggttcaacc tgtagctcca    540
atttaggtgt cagttgcaga cgtaatgtag gagaggagtg agcatcacct actgtgcagc   600
ggagctggga gacatggaaa attggatgaa taagagctga attcgatagc tggagtctga    660
aagcgactac accgattcat tgggaatagg gtatgggcta gcatctagtt ggcagttttt     720
cattggaccg tttggtgagt gaatgctggt tatataattt gattttttagg aagaccttgt     780 ctccccacct taaactcctc ttttcgacgt tttagatcag tatgggcttt catacgttgc     840
tgtgcacgtt agagatgcat gatgcattcc ttaaatcatc acgatctcat tctgtgcctg     900
```

```
aaaactttc    aatagatgaa    accaccgctg    tctcctttt    gtaaggcaaa    ataggtggta      960
gatcttgacc   atataatgct    ttgaaggttg    tggacttgag   ggatgtatta    tgtgctgtat     1020
gaaaaatcag   cccaagataa    accatttagg    ccattgtttg   ctcatatgtg    aaacaatgta     1080
gtaggtacgt   gtcaagacac    ctattaagaa    ccttcaattg   cccttcgatg    gtatggtatg     1140
tggtgctttt   cttgagttgt    tttccttgtt    gcttaataa    atggctccaa    aagttgctca     1200
caaaaattcg   atcgtgatcg    gtaatgatgg    acatggaaat   tcatgtaagt    taacaacttc     1260
gcgcataaaa   gtttcagcta    gtgtttaagc    ttccaaaagt   gatcatggtc    aatctatcaa     1320
caaccaccaa   aatcgtgtcc    ccaacgttgg    atttgggaag   gccttctatg    aatctatgat     1380
tatttcgtcc   caaacttgtg    ctggaagtgg    gagggctgga   gtaatccggt    aggttaagta     1440
ttgaggagtt   tatttgttg     ccccaaaaag    ttcagctgcg   atgtgtttat    aagttttgag     1500
cttgcctaaa   tgtcctcgcc    atggactttt    ttaaaatcag   ctaggatgtg    tggaattatg     1560
gtgggttttc   tttgggatag    ctacttttgt    agtagaggat   gtgttatgga    gagtgaaaac     1620
gtagtgttgt   tgattactga    cgtgaatatc    atatcatagc   tgagtaagga    aggcatcagc     1680
ggaattaata   ctagggtaat    tttagtgggg   gtaatttggt   caagtaaaaa    attcattaca     1740
tgaaattcgg   gtttcccaat    cataatccca    aagctggtgc   aactcagtga    gtaaggaagg     1800
catcagcgga   attaatgcta    gggtaatttt    agtggggta    atttggtcaa    gtgaaaaatt     1860
cattacatga   aattcgggtt    tcccaatcat    aatcccaaag   ctggtgcaac    tcagctttgg     1920
ctctttttt    tctgataaaa    aaaagacgc    ttaagacag     cttggccttt    tggcttctag     1980
ctgcaaaaga   agcttaaatt    aattagagca    atttgcggcg   aaacctcctt    atgttttgat     2040
ttttatacac   ttaaccccct    tatctttat    tttggtggca    aaaccccctt    atgttttaat     2100
ttttatacac   ttaaccccct    tatcttttt    ttggtggcaa    accccttatg    ttttaatttt    2160
tatacactta   acccctctat    cttttgtttt    ggcggcaaaa   cccttcagtt    tactttctt     2220
tgcaaattta   aagttttagt    taaatattac    cgttaaatac   taactagatt    actactgtat     2280
cgacttcgag   gttttaccgt    tacatataca    aaggtgtata   cagtggtcat    ccagttgata     2340
tttaacggta   atatttaact    ggcgtgtcaa    atttggaaag   aaaaataaac    ataaggggggt   2400
tttgccacca   aaaaaagat    aaggggggtta   agtgtataaa   aattaaaaca    taagggagtt    2460
ttgccacaaa   aaaaaagat    aaggggggtta   agtgtataaa   aattaaaaca    taaggggggtt   2520
ttgccaccaa   aaataaagat    aaggggggtta   agtgtataaa   aatcaaaaca    taagggggt     2580
tcgccgcaaa   ttgctcaatt    aattaataag    ccacttttt    ttgttttacc    aaacagtttg    2640
gcatttagct   tattcaacaa    gtgcttttaa    gtttctctaa   aagctgtcta    aatggggcct    2700
agatctctcc   aaagagatct    ctttcaaatc    taaactcttt   caacataacc    gaaactgagt    2760
tctaattctc   tatatataga    ataaagcttg    cgcatcaaca   acttaattaa    aagctactaa    2820
ctaatacaaa   aagaacaact    cagcctaaaa    caattaatga   aagactaaaa    ctgaataaac    2880
tgctttaata   aaacttatgc    ttggcctttt    ctgttttttg   tagacacatt    ggtccagggt    2940
tatcagaaag   cagtctgagc    aagtgatctg    gttgtatttg   tttttttgttt   tacaagttct    3000
gtgactcttg   ttgatgcaat    ttttttttata  tataatcaac   taagttgcct    gcattctaga    3060
aaaactggtg   catctcaagg    ttttgcact    atgttttgc    cttattgtca    tatgtttgaa    3120
cttgcaggtt   ttggaagaga    ttcgggttgg    cctggaatta   aatgactatg    gtatgcagca    3180
gagacgctta   gcccatatgc    gatttttagg    agagctatac   aactatgagc    atgtggattc    3240
gtctgttatt   tttgagacgc    tgtatttgat    tcttgtcttt   ggccatggct    caccagaggt    3300
```

```
attcttctat gtgctcagaa caattgttat gaatctttt tgtttctgac atacatgctt    3360
tgatgtgaaa ataatagatg gaatctcttc ataccaacgg ggttttttc tttttaagttt  3420 tatttataga tgctatttgg gatggtgata cagctaaagt gcgatatgga aaatgatttg   3480
tgtcatttgg ggtgtcatat agctaaaagg agaacatggc ttatggact tgtatgtcaa    3540 aaatgaattt ttaatgacac tatgccatgt ataactatgt ctttgttttt cttaatattt  3600
attttgtttg attttggtg cgaaatatat tatgtaaaaa tattctgaca tggtatctaa    3660 tattatttc ccatctcata gcaagatcta ctagacccac cggaggattg tttccgcatg    3720
aggatggtta ttactctcct tgagacctgt gggcactact ttgatcgagg ctcttctaaa   3780
aggaaacttg atcgatttt aatacacttt caaagatata tcttgagcaa aggtgcttta   3840
ccactggata ttgaatttga tttacaggta tttattgcag tttatttttt taattcatt   3900 tgtagttgtt ctttttgcat gctttgatga ctggaagtaa tattatagca ccgtttatat  3960
tacacctata ttatatgctt gaaatgagaa aacactgaag tctgttatat cccttatgtt  4020
tttgaaaatg tgttgtatct tcattccctt tatgcactca atttattacc ttcctggaat  4080
ttgagggaga tctattgtac tgaagctttc attttcagga tttatttgct gatttacgtc   4140
ccaatatgac tcgatactca tctattgaag aagttacttt agctctggtg gaacttgagg   4200
agcatgaacg tactctccca tctgacaaaa caagtagtga gaagcactct gacagtgaaa   4260
taaggagttc tttcaactct atttcagcaa atggacagag tgctgtgaat ggtaacgagg   4320
gaaatggtag gttgcatgat ggccttggag acagtgacag tgattctgga agcgggactc   4380
ttgatcaaga ggggcgtgat gaagaagaac tggatgatga aatcatgat gaagaatgtg    4440 atactgatga ggaggatgac gatggggtg gacctgcctc agatgaggat gaagtccacg    4500
tgaggcagaa ggtgatggaa gttgaccctc ttgaagcagc aactttgag caagaactaa    4560 aggctgtcat gcaggcaagt gttttttctt taactcttgt ggcatatcat ttaatgtgtt   4620
ttattctgat gactgtggtg tggggcttgt gtgctggtgg tgaatattga ttatttctaa   4680
cgtcaaatta aattaaatgc aggaaagcat ggatcagcgc aggcaagaac tacgtggtcg   4740
acccacatta aatatgatga taccaatgaa cgtgtttgaa ggatcaacca gggggttgg    4800 tggtgaaagt ggtgatgaag cattggatga ggagggtgga ggaattaagg acgtccaggt   4860
aaaagttctt gtgaagcgtg ggagcaagca acagactagg cagatgtaca tccctcggga   4920
ttgctctctt gtacagagca caaaacagaa agaagcagct gagcttgagg agaaacaaga   4980
catcaaaagg ctagtttag aatataatga tagagaggag gaggaactga atgggttggg    5040
aacccaaaca ttgaaccata tgcagggtag cggcagtaga ggttccaccc gaggtcactt   5100
gtgggaagga agcagtggga gggggggaac acgtcatcgg cattattccg gtggtggaat   5160
cttctacaac agaaaaaagt gaaggttatt atgctagaag gctttcttgt ttttgccaca   5220
agttcaaata ggtacagtaa actatctcaa tttctaacga gatttgtcga ggctgcctaa   5280
aacgaagcgg tgccttttct gcaaggctga tgtgccgttt cttaccccat tctgatgagc   5340
tcaatagtct aaaaaaagta gcgcttcggg aaaaatgttt taagaagttc aattgccagg   5400
tagttagtgc gagacacaat gctatgtgtt ttcagtttct gatctgcaat gtacctgtgg   5460
gatttgattg tgtgctgtat agatcctgcg tttggcattt gctgcagttt gcatgtatat   5520
atattatgta agacaaaatg aagatagtat gaccaaaaat ctcttgcttt gttcttattt   5580
tagatatagt gtaatgattt ctgttatact tgtgtagtga ctgactcatt caaaccgaac   5640
```

```
ttaatatgca tttagaatgg ttgagagttt atgataatga taatgcaata ccaatttcat    5700
atgaccaatt cctctattgt atccatattg ttttggacag ttaatgtgtt gtaatggtac    5760
tcatcgtttt agttgcccca cggctacaaa tgttttcaaa tcgtttcgag tccaattggg    5820
taaggtgtgg taattaaaac aaatctataa tgataatgta ataccaacct tatacgacca    5880
attcttgtat ggtatccata ttgttttgga cagttgtttt tttttttttct tgtaatggta    5940 ctcaccgttt cagttgtcca atgttttcaa atcgtgtttt gagtccaatt ggaaaaggtg    6000
tggtagtttt aataaatcta tatggagttt                                     6030
```

<210> SEQ ID NO 2
<211> LENGTH: 171
<212> TYPE: DNA
<213> ORGANISM: Cannabis sativa

<400> SEQUENCE: 2

```
aatgtgttgt aatggtactc atcgttttag ttgccccacg gctacaaatg ttttcaaatc     60
gttcgagttc caattgggta aggtgtggta attaaaacaa atctataatg ataatgtaat    120
accaacctat acgaccaatt cttgtatggt atccatattg ttttgacagt t             171
```

<210> SEQ ID NO 3
<211> LENGTH: 24
<212> TYPE: DNA
<213> ORGANISM: Cannabis sativa

<400> SEQUENCE: 3

```
gtacagtaaa ctatctcaat ttct                                            24
```

<210> SEQ ID NO 4
<211> LENGTH: 24
<212> TYPE: DNA
<213> ORGANISM: Cannabis sativa

<400> SEQUENCE: 4

```
accacacctt ttccaattgg actc                                            24
```

<210> SEQ ID NO 5
<211> LENGTH: 210
<212> TYPE: DNA
<213> ORGANISM: Cannabis sativa

<400> SEQUENCE: 5

```
gctactggaa acctgtctat tttctagtgc aatgaagtat aatatggaca atgaggcaag     60
gcaatgtaag taggttaaga gataaaagtt tcaaggcact ggaaaaggaa tggaaagtat    120
aatcatagtt aggcagagaa agatttgaac tgttatacgg ttcttttatg ggatgggagt    180
ttattatgaa tttcaagtgg agaaaaaaaa                                     210
```

<210> SEQ ID NO 6
<211> LENGTH: 201
<212> TYPE: DNA
<213> ORGANISM: Cannabis sativa

<400> SEQUENCE: 6

```
aacactcaac acacaaatat acaaatatca aatacacata cactcacaca cacaaatggt     60
aatgaaagaa agaagacggt accttaaaag cagaacgagc gacatagccc aggcgttgag    120
cttctctgta gaaaaaatct ggagctccag ctccactcat ctctgcaaat gttaaaaccc    180
taaaccccgg tagtcgcaca g                                              201
```

<210> SEQ ID NO 7
<211> LENGTH: 201
<212> TYPE: DNA
<213> ORGANISM: Cannabis sativa

<400> SEQUENCE: 7

| | |
|---|---|
| ctggcggtgc ccaaaatttt gggcacccgg ttgaaaattt gattgcctgg ttgggaactt | 60 |
| tttcgagtat ctcaattttt gtgatattta ggatattgac tcttcattta tggatggaaa | 120 |
| aattttaaat tataaattta agttgtaaaa agtatttag tgagacatat accaatttac | 180 |
| cattaaatat tttctactac t | 201 |

<210> SEQ ID NO 8
<211> LENGTH: 201
<212> TYPE: DNA
<213> ORGANISM: Cannabis sativa

<400> SEQUENCE: 8

| | |
|---|---|
| gttatatgga gacttcacat ccaccactaa caacgtggcc atgatggtgg ttaccttgg | 60 |
| gctagtgctg ctagtgagtg cagtttgat cttgccacat ggagtaatgg cagctccact | 120 |
| gaaaccatac attagatgtt cgcatggatt taggtgtttg agtgacaaac caatctggat | 180 |
| taaagtttgc ttgaataaga t | 201 |

<210> SEQ ID NO 9
<211> LENGTH: 201
<212> TYPE: DNA
<213> ORGANISM: Cannabis sativa

<400> SEQUENCE: 9

| | |
|---|---|
| cctccttgtt tttacataat caatgcatgc cttattcttc ttttacttta tctttatttt | 60 |
| tttttcttta aaattacatt ttctttagtt tattggtgat atcccttcta gcttagcata | 120 |
| attttgcctg tactattaag gcaatcaaat tttgtcttca ttttacaat ttagtattt | 180 |
| tcttgtactg aataagattt t | 201 |

<210> SEQ ID NO 10
<211> LENGTH: 201
<212> TYPE: DNA
<213> ORGANISM: Cannabis sativa

<400> SEQUENCE: 10

| | |
|---|---|
| gtgtctccct aaatcccgtg ggagccttgg cttccgaaaa actaagaaaa tgaatcagga | 60 |
| ttcttggct aagtaggctt ggaaactgct tactaaatcc caatctttgt gttgaagaat | 120 |
| tctaagagct aaataccta gaggaaagga tatgcttaag tgtaaggcta agtctgttga | 180 |
| cttttggttt tagaaaagtg t | 201 |

<210> SEQ ID NO 11
<211> LENGTH: 201
<212> TYPE: DNA
<213> ORGANISM: Cannabis sativa

<400> SEQUENCE: 11

| | |
|---|---|
| ccttcagatt ataatacaaa acacaataag aaatttgaaa atacagataa agaagcaata | 60 |
| tataaccatg tggaactgtt caagtatgtc tacgcaatca acattaccgg atttccatca | 120 |
| gaatctccaa agccttttt gggaccatat taatagattg caactgaaaa tttccatgtc | 180 |

```
aacattagta gaagaagatc a                                            201
```

<210> SEQ ID NO 12
<211> LENGTH: 201
<212> TYPE: DNA
<213> ORGANISM: Cannabis sativa

<400> SEQUENCE: 12

```
tttaaatgag taatttaatt tcatgttatt atacgtaaaa aaaatatat gtatatatat    60
gaaaattaac attaaaattt tacttttat ttttggatta gatttatcca attcaatcca   120
ataaatacta gatctaaatt attggatgaa tctaattcga tccataaata ttaggtgtaa  180
aatattagat aaacttgaat t                                            201
```

<210> SEQ ID NO 13
<211> LENGTH: 201
<212> TYPE: DNA
<213> ORGANISM: Cannabis sativa

<400> SEQUENCE: 13

```
actggtttaa tatataaata tataaaataa tataaaattt aaaagaagaa gaatataaag   60
agagaaaaaa attaaatgaa aatttttcag ttagagtgaa ttcttattta tacaaaaata  120
tgattaaaag aatgaaaaat taaactaatg taataaagaa aaatacaact aagcattaat  180
ggcgataatt aatttggtga t                                            201
```

<210> SEQ ID NO 14
<211> LENGTH: 201
<212> TYPE: DNA
<213> ORGANISM: Cannabis sativa

<400> SEQUENCE: 14

```
ctaagtttga gatgaaggac ttaggaaatg ccacttaaat ccttggaata attattgtga   60
gggataaagg caagggatcc taaagatgtg tcaggaagat aacattcaga aggtgattga  120
gaagtgttgg gaatatttta ctaggatcta gatttactaa caagtatgat gattaacatc  180
ctaaatatga atatctctaa a                                            201
```

<210> SEQ ID NO 15
<211> LENGTH: 373
<212> TYPE: DNA
<213> ORGANISM: Cannabis sativa

<400> SEQUENCE: 15

```
aatatgcatt tagaatggtt gagagtttat gataatgata atgcaatacc aatttcatat   60
gaccaattcc tctattgtat ccatattgtt ttggacagtt aatgtgttgt aatggtactc  120
atcgttttag ttgccccacg gctacaaatg ttttcaaatc gtttcgagtc caattgggta  180
aggtgtggta attaaaacaa atctataatg ataatgtaat accaacctta tacgaccaat  240
tcttgtatgg tatccatatt gttttggaca gttgtttttt ttttttcttg taatggtact  300
caccgtttca gttgtccaat gttttcaaat cgtgttttga gtccaattgg aaaaggtgtg  360
gtagttttaa taa                                                     373
```

<210> SEQ ID NO 16
<211> LENGTH: 201
<212> TYPE: DNA
<213> ORGANISM: Cannabis sativa

<400> SEQUENCE: 16

```
attgattata aaataaatag agcttaagaa acaaaaaaat taaagaagaa gaaaactaag      60 attttttacgt ggttggagcg ttgatgaact ttagtccacg agtccatata ttattaattt    120
gagaaacttt gatgttttac acaaggataa tatttttttcc aaacttaaga accctaattt   180
aagtcttagt atttgaataa t                                              201
```

<210> SEQ ID NO 17
<211> LENGTH: 201
<212> TYPE: DNA
<213> ORGANISM: Cannabis sativa

<400> SEQUENCE: 17

```
ataaatagag cttaagaaac aaaaaaatta agaagaaga aaactaagat ttttacgtgg      60
ttggagcgtt gatgaacttt agtccacgag tccatatatt attaatttga gaaactttga   120
tgttttacac aaggataata ttttttccaa acttaagaac cctaatttaa gtcttagtat   180
ttgaataatg attttccacc a                                              201
```

<210> SEQ ID NO 18
<211> LENGTH: 201
<212> TYPE: DNA
<213> ORGANISM: Cannabis sativa

<400> SEQUENCE: 18

```
aaaattaaag aagaagaaaa ctaagatttt tacgtggttg gagcgttgat gaactttagt    60
ccacgagtcc atatattatt aatttgagaa actttgatgt tttacacaag gataatattt   120
tttccaaact taagaaccct aatttaagtc ttagtatttg aataatgatt ttccaccatt   180
tgcatgaaga tacaatcttc t                                              201
```

<210> SEQ ID NO 19
<211> LENGTH: 201
<212> TYPE: DNA
<213> ORGANISM: Cannabis sativa

<400> SEQUENCE: 19

```
aagattttta cgtggttgga gcgttgatga actttagtcc acgagtccat atattattaa     60
tttgagaaac tttgatgttt tacacaagga taatattttt tccaaactta agaaccctaa   120
tttaagtctt agtatttgaa taatgatttt ccaccatttg catgaagata caatcttcta   180
ttataggcta gggttaagac a                                              201
```

<210> SEQ ID NO 20
<211> LENGTH: 201
<212> TYPE: DNA
<213> ORGANISM: Cannabis sativa

<400> SEQUENCE: 20

```
ggttggagcg ttgatgaact ttagtccacg agtccatata ttattaattt gagaaacttt    60
gatgttttac acaaggataa tatttttcc aaacttaaga accctaattt aagtcttagt   120
atttgaataa tgattttcca ccatttgcat gaagatacaa tcttctatta taggctaggg   180
ttaagacagt taggattttt g                                              201
```

<210> SEQ ID NO 21
<211> LENGTH: 201
<212> TYPE: DNA
<213> ORGANISM: Cannabis sativa

<400> SEQUENCE: 21

```
gttttacaca aggataatat tttttccaaa cttaagaacc ctaatttaag tcttagtatt      60
tgaataatga ttttccacca tttgcatgaa gatacaatct tctattatag ctagggtta     120 agacagttag gattttttgta tgaagctaaa cccactgaag gagtaaatac atttaatagt    180
gactttagat taattagaaa a                                               201
```

<210> SEQ ID NO 22
<211> LENGTH: 201
<212> TYPE: DNA
<213> ORGANISM: Cannabis sativa

<400> SEQUENCE: 22

```
ttacacaagg ataatatttt ttccaaactt aagaaccta atttaagtct tagtatttga      60
ataatgattt tccaccattt gcatgaagat acaatcttct attataggct agggttaaga    120
cagttaggat ttttgtatga agctaaaccc actgaaggag taaatacatt taatagtgac    180
tttagattaa ttagaaaaga a                                               201
```

<210> SEQ ID NO 23
<211> LENGTH: 201
<212> TYPE: DNA
<213> ORGANISM: Cannabis sativa

<400> SEQUENCE: 23

```
acttaagaac cctaatttaa gtcttagtat ttgaataatg attttccacc atttgcatga     60
agatacaatc ttctattata ggctaggggtt aagacagtta ggattttttgt atgaagctaa    120 acccactgaa ggagtaaata catttaatag tgactttaga ttaattagaa aagaactcat    180
ttacaagata acgatcatct a                                               201
```

<210> SEQ ID NO 24
<211> LENGTH: 201
<212> TYPE: DNA
<213> ORGANISM: Cannabis sativa

<400> SEQUENCE: 24

```
cttaagaacc ctaatttaag tcttagtatt tgaataatga ttttccacca tttgcatgaa     60
gatacaatct tctattatag ctagggtta agacagttag gattttttgta tgaagctaaa   120 cccactgaag gagtaaatac atttaatagt gactttagat taattagaaa agaactcatt    180
tacaagataa cgatcatcta t                                               201
```

<210> SEQ ID NO 25
<211> LENGTH: 201
<212> TYPE: DNA
<213> ORGANISM: Cannabis sativa

<400> SEQUENCE: 25

```
catttggtta ttatatatat attcatgatt tttttttttc tatttattac tattgacaat    60
gttgttattt tagttatttc aaacttttaa ttgcattaca cttgtaagga taatattttt    120
atggagtatt aaatataaat aaagagtgat atttaattt tatgtatttt tcttcatatt    180
tggaaattaa tactaaaaat t                                               201
```

<210> SEQ ID NO 26
<211> LENGTH: 201
<212> TYPE: DNA
<213> ORGANISM: Cannabis sativa

```
<400> SEQUENCE: 26
acttgttata aattatagtt gaacttcttt atattgttat tgctcaaata gaagttaaca      60
attatacaag tcttatacat tatgggttca gaaactttga ttgaagtgat attggctata     120
ctccttcctc cagtgggtgt tttcctccgc tttggttgtg cggtaataat taatcttaaa     180
tatcttatta tgtctatgcc a                                               201

<210> SEQ ID NO 27
<211> LENGTH: 201
<212> TYPE: DNA
<213> ORGANISM: Cannabis sativa

<400> SEQUENCE: 27
caaggtctgc tcaattcctt gatcatcaag caatctcaat tccttgatca tcaagcaatt      60
tatcagtagt gttgttagtg ggtttgctat tagcttttg gtaaaaaaaa aaaaaaaaa       120 aaaaaaaaaa cgagtgttcg agtctcctaa tttgagccaa aaaacacgag accgttgttg     180
gcaataatcc tcttcttaag c                                               201

<210> SEQ ID NO 28
<211> LENGTH: 201
<212> TYPE: DNA
<213> ORGANISM: Cannabis sativa

<400> SEQUENCE: 28
aagaaggagg tttcggcatc aaagattcag agaaagagat ccaggttcag atattgataa      60
tgctctgcta cagaaaggaa tcaagggcta gatatctgaa cggaaggagt cattatattc     120
cgctgcaacc aatgtaaggt ttcctaaact ttatatgtgt ttatttcatc gttttagaaa     180
gttcatattt agggtgttaa t                                               201

<210> SEQ ID NO 29
<211> LENGTH: 201
<212> TYPE: DNA
<213> ORGANISM: Cannabis sativa

<400> SEQUENCE: 29
tttttctccc atctgattca aatgtaatat tttgattgaa attcactcaa ataagaggaa      60
gacagagaag gagtgaaaag accaagattg gcagagttat tataccaaac aagaaaagag     120
caaaatacta acatgtaagg atattaagac aaagacaatt tagtgatgaa acttacagaa     180
gctctgaact tatcaatctc t                                               201

<210> SEQ ID NO 30
<211> LENGTH: 201
<212> TYPE: DNA
<213> ORGANISM: Cannabis sativa

<400> SEQUENCE: 30
ttgacacaac acgaaactgg cacgagcaca attagacacg aaaaaatatg ggcattagca      60
cgacataggc acgacaaaag atgaaaaata tgtccttaag tacaatacga cacgagaagt     120
agggctgaac atttaaaccc gcaaacccga aacccggca acccaccccg acccgctgcc     180
gaaaaaaaac cgaaaaattg a                                               201

<210> SEQ ID NO 31
<211> LENGTH: 201
<212> TYPE: DNA
```

<213> ORGANISM: Cannabis sativa

<400> SEQUENCE: 31

| acctttgaaa gggatccttt cattttgaac atgaacttat tgtctcttat accgtcaaga | 60 |
| atttaattaa ttctccataa taaaaaagta ttgaatgagt ggtttggtgg taaaatgctt | 120 |
| actctcaact agttttttaa gccgttaaat ataagaaaaa tgtctcgcag cttagccacc | 180 |
| ctagacatcc attttaggca c | 201 |

<210> SEQ ID NO 32
<211> LENGTH: 201
<212> TYPE: DNA
<213> ORGANISM: Cannabis sativa

<400> SEQUENCE: 32

| tttgattgtt tttttaaaat aagataaaaa gataaaatag aaatatttat gaaaataaag | 60 |
| aattatataa gtgaaaatgt tttagacaaa acgtaaaaat taaaaaaaaa aaaaaaaaaa | 120 |
| aaaaaaaaaa aaaaaggagt acaacggttt atgcaaacgt gtataattaa cctaataatt | 180 |
| ataataagaa tagaattagg a | 201 |

<210> SEQ ID NO 33
<211> LENGTH: 201
<212> TYPE: DNA
<213> ORGANISM: Cannabis sativa

<400> SEQUENCE: 33

| aagaagttga acctcctcat gagacaaaga caaatagtag ttctttgact gatcttcaaa | 60 |
| gaagcattat aaaagaatta ttagaaatca tatcgtctcc tattgaaaat aaacaacaac | 120 |
| aagatcaatc taatgaagtt gataaaataa ttattcaaga tgatggcata ggcctcgatg | 180 |
| atctccctga ggaattcttc a | 201 |

<210> SEQ ID NO 34
<211> LENGTH: 201
<212> TYPE: DNA
<213> ORGANISM: Cannabis sativa

<400> SEQUENCE: 34

| atttttatg aatcttaaat tcaaattctt tttttaatgt tttatatggt tttttttttt | 60 |
| tttttagttt aattggttaa ataatgtcat atttagtggc atttacttt tatgtcatat | 120 |
| ttatcataac cttaataatt ttttccatat tttttaaaat agcccatcaa attttgtccc | 180 |
| cgaatgttaa gcggggcggg a | 201 |

<210> SEQ ID NO 35
<211> LENGTH: 201
<212> TYPE: DNA
<213> ORGANISM: Cannabis sativa

<400> SEQUENCE: 35

| aataataaat aaaaacttta acaaaaaaaa ttaattaaaa aattattcga actttaaatt | 60 |
| aattttaata aactaaccaa tttcatgagt tactaataat gttttattaa tttatattta | 120 |
| aaagttaatc ttgtatcttt gctaaacttg tattatagag caattttaat agatttttaa | 180 |
| aattatttat aaaagtatta a | 201 |

<210> SEQ ID NO 36
<211> LENGTH: 201

<212> TYPE: DNA
<213> ORGANISM: Cannabis sativa

<400> SEQUENCE: 36

```
aaataattat tatttagttt tgataataaa gttattggta agatttcata tatatacata    60
ttattaataa cttttatat ttgattataa tttattaatt tcttaaatat taattaacat   120
gaaaaaatta ctaaataaag taacataaat atatcttaaa ttagcaatca atttcatggg   180
ttacttaaaa ttatttttat t                                            201
```

<210> SEQ ID NO 37
<211> LENGTH: 201
<212> TYPE: DNA
<213> ORGANISM: Cannabis sativa

<400> SEQUENCE: 37

```
taattaaatt tcttaatttg taactaatct ataagaagtc atgaaaagaa aaaatattt     60
aagaaaattg gtaagcaaat ttataattca tataataata atagattgat gtaaattata   120
gagaaaagta aaactcaata ccaaattaca ataaatctta aattataaat gttagatcgt   180
aagtagacca aacaaaaaaa a                                            201
```

<210> SEQ ID NO 38
<211> LENGTH: 201
<212> TYPE: DNA
<213> ORGANISM: Cannabis sativa

<400> SEQUENCE: 38

```
acataaatta attaataact atatactgat tgaataaaga ggataagaaa aaacttatca    60
catcaaaatg atctccaaat cttcattatt tttaaatatc ccatttgttt cgaacattgt   120
tatatatcta ctttgttcca cctacaccac ttagacgaaa cccaatgcag tttgctaacg   180
ttaaagatta gccaatttag t                                            201
```

<210> SEQ ID NO 39
<211> LENGTH: 201
<212> TYPE: DNA
<213> ORGANISM: Cannabis sativa

<400> SEQUENCE: 39

```
tgattgaata aagaggataa gaaaaaactt atcacatcaa aatgatctcc aaatcttcat    60
tattttaaa tatcccattt gtttcgaaca ttgttatata tctactttgt tccacctaca   120
ccacttagac gaaacccaat gcagtttgct aacgttaaag attagccaat ttagtttaca   180
ttttcattac attttgctct a                                            201
```

<210> SEQ ID NO 40
<211> LENGTH: 201
<212> TYPE: DNA
<213> ORGANISM: Cannabis sativa

<400> SEQUENCE: 40

```
tgattattcg gattgaaaca atagataatt tatagcgtat ctattcttgg tgaatagagt    60
attttatgta atcaggagtg caatttcgaa tctatagttg agtgaggagg aattaataat   120
aaagaaaatt tacttgataa attctagaat tacttattga gtgcttgatt ataggccc    180
atgtccttgt actagttgag a                                            201
```

<210> SEQ ID NO 41

```
<211> LENGTH: 201
<212> TYPE: DNA
<213> ORGANISM: Cannabis sativa

<400> SEQUENCE: 41
ggaattaata ataaagaaaa tttacttgat aaattctaga attacttatt gagtgcttga      60
ttatataggc ccatgtcctt gtactagttg agataataat gtcttgtaga ctcaattaat     120
taattttaat taatcaatta gaattctatt tatgagtttc actaagtaag ggcttatttg     180
agaagaaaat gaggatttaa g                                                201

<210> SEQ ID NO 42
<211> LENGTH: 201
<212> TYPE: DNA
<213> ORGANISM: Cannabis sativa

<400> SEQUENCE: 42
aaggtacaat ctatgctact atattttaaa atattcatta tacattgtaa atattgaaat      60
atgtaaattt tttacttata tttcaggttg aaagtatata tgtttatata tgcacacacg     120
tctataatga aaggttttg ttttaatttc aatttcaaga ataaaaatta cagtaattta     180
aattgaattc atatctttct t                                                201

<210> SEQ ID NO 43
<211> LENGTH: 201
<212> TYPE: DNA
<213> ORGANISM: Cannabis sativa

<400> SEQUENCE: 43
atctatgcta ctatatttta aaatattcat tatacattgt aaatattgaa atatgtaaat      60
tttttactta tatttcaggt tgaaagtata tatgtttata tatgcacaca cgtctataat     120
gaaaggtttt tgttttaatt tcaatttcaa gataaaaat tacagtaatt taaattgaat     180
tcatatcttt cttttaatta c                                                201

<210> SEQ ID NO 44
<211> LENGTH: 201
<212> TYPE: DNA
<213> ORGANISM: Cannabis sativa

<400> SEQUENCE: 44
catattttaa tagtggtata tataatttttg ttagcatgat atatatttttt tgagtattaa     60 tttagtattg tttataatttt tttgtggtat ataattttat cactatagta tattaatttt     120
cagtaatacg atatatcaaa tactgctgta tatatttaat gatctaatat tttattcatt     180
ttgttacaat ataataatat g                                                201

<210> SEQ ID NO 45
<211> LENGTH: 22
<212> TYPE: DNA
<213> ORGANISM: Cannabis sativa

<400> SEQUENCE: 45
ctaaaaaaag tagcgcttcg gg                                                22

<210> SEQ ID NO 46
<211> LENGTH: 24
<212> TYPE: DNA
<213> ORGANISM: Cannabis sativa

<400> SEQUENCE: 46
```
tgtagccgtg gggcaactaa aacg                                          24

<210> SEQ ID NO 47
<211> LENGTH: 10
<212> TYPE: DNA
<213> ORGANISM: Cannabis sativa

<400> SEQUENCE: 47
ggaaaaggaa                                                          10

<210> SEQ ID NO 48
<211> LENGTH: 10
<212> TYPE: DNA
<213> ORGANISM: Cannabis sativa

<400> SEQUENCE: 48
gagaaaagaa                                                          10

<210> SEQ ID NO 49
<211> LENGTH: 173
<212> TYPE: DNA
<213> ORGANISM: Cannabis sativa

<400> SEQUENCE: 49
aatgtgttgt aatggtactc atcgttttag ttgccccacg gctacaaatg ttttcaaatc   60
gtttcgagtc caattgggta aggtgtggta attaaaacaa atctataatg ataatgtaat  120
accaacctta tacgaccaat tcttgtatgg tatccatatt gttttggaca gtt         173

<210> SEQ ID NO 50
<211> LENGTH: 171
<212> TYPE: DNA
<213> ORGANISM: Cannabis sativa

<400> SEQUENCE: 50
aatgtgttgt aatggtactc atcgttttag ttgccccacg gctacaaatg ttttcaaatc   60
gttcgagttc caattgggta aggtgtggta attaaaacaa atctataatg ataatgtaat  120
accaacctat acgaccaatt cttgtatggt atccatattg ttttgacagt t           171

<210> SEQ ID NO 51
<211> LENGTH: 13
<212> TYPE: DNA
<213> ORGANISM: Cannabis sativa

<400> SEQUENCE: 51
attataggct agg                                                      13

<210> SEQ ID NO 52
<211> LENGTH: 14
<212> TYPE: DNA
<213> ORGANISM: Cannabis sativa

<400> SEQUENCE: 52
atttataggc tagg                                                     14

<210> SEQ ID NO 53
<211> LENGTH: 13
<212> TYPE: DNA
<213> ORGANISM: Cannabis sativa

<400> SEQUENCE: 53

```
atttagccgc taa                                                          13

<210> SEQ ID NO 54
<211> LENGTH: 14
<212> TYPE: DNA
<213> ORGANISM: Cannabis sativa

<400> SEQUENCE: 54
atttatacgc tagg                                                         14
```

METHODS OF DETERMINING SENSITIVITY TO PHOTOPERIOD IN CANNABIS

CROSS-REFERENCES TO RELATED APPLICATIONS

This application is a continuation of U.S. patent application Ser. No. 17/439,757, filed Sep. 15, 2021, which is a national stage of International Application No. PCT/CA2021/050442, filed Mar. 31, 2021, the disclosures of which are incorporated herein by reference in their entirety, which claim priority to Canadian Patent Application No, 3077823, filed Apr. 1, 2020.

STATEMENT REGARDING SEQUENCE LISTING

The sequence listing associated with this application is the same sequence listing filed in U.S. patent application Ser. No. 17/439,757, is provided in text format in lieu of a paper copy, and is hereby incorporated by reference into the specification. The name of the text file containing the sequence listing is 1018-P14USCON_Seq_List_20221129_ST25.txt. The text file is 25 KB and was created on Nov. 29, 2022.

FIELD OF THE DISCLOSURE

This disclosure relates to the field of genetic markers for an day length neutral phenotype in *Cannabis*. More specifically, this disclosure relates to methods and compositions useful for identifying individual plants that display a day length neutral phenotype, or are a carrier for that trait.

BACKGROUND OF THE DISCLOSURE

Much of the cannabis in production today is day length (photoperiod) sensitive, meaning that it initiates flowering only after a transition from long photoperiod days to short photoperiod days. This has several limitations, especially at more northern (and more southern) latitudes.

SUMMARY OF THE INVENTION

The present disclosure pertains to an about 20 megabase region containing about 1,172 genes, any of which could be a causative gene responsible for the day length neutral phenotype in *Cannabis*. For example, the present disclosure pertains to the utility of an allele at a polymorphic site in an about 20 megabase region located in chromosome CM010796.2 between about 40 megabases and about 60 megabases, and alleles of additional polymorphic sites in linkage disequilibrium with this allele, for identifying *Cannabis* plants that have a day length neutral (i.e. have an "autoflowering") phenotype. In some embodiments, the region is any one of about 1 megabase, about 2.5 megabases, about 5 megabases, about 7.5 megabases, about 10 megabases, about 12.5 megabases, about 15 megabases, about 17.5 megabases, or about 20 megabases located in chromosome CM010796.2 between about 40 megabases and about 60 megabases and the disclosure pertains to the utility of an allele at a polymorphic site in any of these regions, and alleles of additional polymorphic sites in linkage disequilibrium with this allele, for identifying *Cannabis* plants that have a day length neutral (i.e. have an "autoflowering") phenotype. For example, the *Cannabis* UPF2 gene is within an about 1 megabase region and contains 46 additional genes and numerous mutations, any of which could be the causative allele responsible for the day length neutral phenotype.

Various aspects of the disclosure relate to the utility of an allele at a polymorphic site within an about 20 megabase region in *Cannabis* chromosome CM010796.2 located between about 40 megabases to about 60 megabases and alleles of additional polymorphic sites in linkage disequilibrium with the allele, for identifying *Cannabis* plants that have a day length neutral (i.e. have an "autoflowering") phenotype. In some embodiments, the polymorphic site is in the *Cannabis* UPF2 gene, and alleles of additional polymorphic sites in linkage disequilibrium with this allele in UPF2, for identifying *Cannabis* plants that have a day length neutral (i.e. have an "autoflowering") phenotype.

Various aspects of the disclosure relate to a method comprising testing nucleic acid from a *Cannabis* plant to determine the presence or absence of a variation in a polymorphic site within an about 20 megabase region in *Cannabis* chromosome CM010796.2 located between about 40 megabases to about 60 megabases. In some embodiments, the disclosure relates to a method comprising testing nucleic acid from a Cannais to determine the presence or absence of a variation in a polymorphic site within the endogenous UPF2 gene. The methods are for identifying whether or not the *Cannabis* plant has a day length neutral phenotype, or is a carrier of a trait for the day length neutral phenotype. The presence of the variation indicates that the plant has the day length neutral phenotype or is a carrier of the trait for the day length neutral phenotype.

Various aspects of the disclosure relate to a method comprising testing nucleic acid from a *Cannabis* plant to determine the presence or absence of an allele that is in linkage disequilibrium $r^2=0.9$ to 1 with a variation in a polymorphic site within an about 20 megabase region in *Cannabis* chromosome CM010796.2 located between about 40 megabases to about 60 megabases. For example, various aspects of the disclosure relate to a method comprising testing nucleic acid from a *Cannabis* plant to determine the presence or absence of an allele that is in linkage disequilibrium variation $r^2=0.9$ to 1 with a variation in the endogenous UPF2 gene.

Various aspects of the disclosure relate to a method comprising testing nucleic acid from a *Cannabis* plant to determine the presence or absence of an allele at a polymorphic site as indicated for any one or more of the example nucleotide sequences identified in Table 1, 2, 3, or 4.

Various aspects of the disclosure relate to a method comprising testing nucleic acid from a *Cannabis* plant to determine the presence or absence of a first allele that is in linkage disequilibrium $r^2=0.9$ to 1 with a second allele at a polymorphic site as indicated for any one or more of the example nucleotide sequences identified in Table 1, 2, 3, or 4.

Various aspects of the disclosure relate to a method of producing a *Cannabis* plant with a day length neutral phenotype. The method comprises performing a first cross of a first parent having at least one allele associated with a day length neutral phenotype at a polymorphic site within an about 20 megabase region in *Cannabis* chromosome CM010796.2 located between about 40 megabases to about 60 megabases (for example, without limitation, any one of the example nucleotide sequences identified in Table 1, 2, 3, or 4) with a second parent that has the day length sensitive phenotype. The method further comprises identifying a first progeny plant from the first cross that has the day length neutral phenotype, or that is a carrier of a trait for the day length neutral phenotype, according to the methods described herein.

Various aspects of the disclosure relate to a method of producing a *Cannabis* plant with a day length neutral phenotype. The method comprising performing a first cross of a first parent that has the day length neutral phenotype and is homozygous for at least one allele associated with the day length neutral phenotype at a polymorphic site within an about 20 megabase region in *Cannabis* chromosome CM010796.2 located between about 40 megabases to about 60 megabases (for example, without limitation, any one of the nucleotide sequences identified in Table 1, 2, 3, or 4) with a second parent that has the day length sensitive phenotype to produce $F_1$ progeny. The method further comprises selfing the $F_1$ progeny to produce $F_2$ progeny. The method further comprises identifying an $F_2$ progeny plant that has the day length neutral phenotype, or that is a carrier of a trait for the day length neutral phenotype, according to the methods described herein.

Various aspects of the disclosure relate to a method of producing a *Cannabis* plant with a day length neutral phenotype. The method comprises identifying a first parent homozygous for at least one allele associated with the day length neutral phenotype at a polymorphic site within an about 20 megabase region in *Cannabis* chromosome CM010796.2 located between about 40 megabases to about 60 megabases (for example, without limitation, any one of the nucleotide sequences identified in Table 1, 2, 3, or 4) according to the methods described herein. The method further comprises crossing the first parent with a second parent that has the day length sensitive phenotype to produce $F_1$. The method further comprises selfing the $F_1$ progeny to produce $F_2$ progeny. The method further comprises identifying an $F_2$ progeny plant that has the day length neutral phenotype.

Various aspects of the disclosure relate to a method of producing a *Cannabis* plant with a day length neutral phenotype. The method comprises performing a first cross of a first parent identified having at least one loss or gain of function mutation allele of one or more endogenous genes (for example, without limitation, the UPF2 gene) within an about 20 megabase region in *Cannabis* chromosome CM010796.2 located between about 40 megabases to about 60 megabases according to the methods described herein with a second parent that has the day length sensitive phenotype. The method further comprises performing a second cross of a first progeny of the first cross with a second progeny of the first cross to produce a plant that is homozygous for the loss or gain of function mutation allele.

Various aspects of the disclosure relate to a method for producing a day length neutral *Cannabis* plant. The method comprises decreasing the expression of one or more endogenous genes within an about 20 megabase region in *Cannabis* chromosome CM010796.2 located between about 40 megabases to about 60 megabases (for example, without limitation, an endogenous UPF2 gene) in the plant.

Various aspects of the disclosure relate to a method of method of generating a *Cannabis* plant having a day length neutral phenotype. The method comprises i) using a molecular methodology to identify a first plant as comprising a loss or gain of function allele in one or more endogenous genes within an about 20 megabase region in *Cannabis* chromosome CM010796.2 located between about 40 megabases to about 60 megabases (for example, without limitation, the UPF2 gene); ii) performing a first cross of said first plant to a second plant; iii) performing a second cross of progeny from the first cross; and iv) screening progeny of the second cross for a plant that is homozygous for the loss or gain of function allele in the endogenous gene.

Various aspects of the disclosure relate to a *Cannabis* plant or plant cell generated according to the methods described herein, as well as seed, plant material, or dried flower of such plants.

Various aspects of the disclosure relate to a genetically modified *Cannabis* plant or plant cell having a day length neutral phenotype, as well as seed, plant material, or dried flower of such plants. The *Cannabis* plant or plant cell is genetically modified to have reduced expression of one or more endogenous genes within an about 20 megabase region in *Cannabis* chromosome CM010796.2 located between about 40 megabases to about 60 megabases (for example, without limitation, the UPF2 gene).

Various aspects of the disclosure relate to an allele-specific polynucleotide for use in the methods described herein.

Various aspects of the disclosure relate to a kit for use in the methods defined herein. The kit comprises at least one allele-specific polynucleotide as descried herein and at least one further component, wherein the at least one further component is a buffer, deoxynucleotide triphosphates (dNTPs), an amplification primer pair, an enzyme, or any combination thereof.

Various aspects of the disclosure relate to a cannabinoids and/or produced by a plant or plant cell as described herein.

Various aspects of the disclosure relate to cannabinoids and/or terpenes extracted or isolated from dried flower as described herein.

Various aspects of the disclosure relate to extracts, concentrates, isolates, or oils of a cannabis plant, plant cell, dried flower, plant material, or seed as described herein. The extracts, concentrates, isolates, and oils comprise cannabinoids and/or terpenes.

Various aspects of the disclosure relate to an expression vector for generating a day length neutral *Cannabis* plant, the expression vector comprising a nucleic acid comprising a portion of SEQ ID NO. 1.

Various aspects of the disclosure relate to use of a polynucleotide molecule having a sequence comprising a portion of SEQ ID NO: 1 for generating a *Cannabis* plant with a day length neutral phenotype.

Various aspects of the disclosure relate to use of a plant or plant cell as described herein for the production of cannabinoids and/or terpenes.

Various aspects of the disclosure relate to a food item comprising a cannabis plant or plant cell, seed, plant material, or dried flower as described herein.

Various aspects of the disclosure relate to a food item comprising extracts, concentrates, isolates, or oils of a cannabis plant, plant cell, dried flower, plant material, or seed as described herein. The food item comprises cannabinoids and/or terpenes.

Various aspects of the disclosure relate to a topical comprising extracts, concentrates, isolates, or oils of a cannabis plant, plant cell, dried flower, plant material, or seed as described herein. The topical comprises cannabinoids and/or terpenes.

Various aspects of the disclosure relate to a pharmaceutical composition comprising extracts, concentrates, isolates, or oils of a cannabis plant, plant cell, dried flower, plant material, or seed as described herein. The pharmaceutical composition comprises cannabinoids and/or terpenes.

Various aspects of the disclosure relate to a method of producing oil. The method comprises crushing seed or plant material as defined herein to release the oil.

Various aspects of the disclosure relate to a method of producing oil. The method comprises extracting oil from a plant or plant cell as described herein.

Various aspects of the disclosure relate to a method of producing an extract comprising a cannabinoid and/or a terpene. The method comprises extracting the cannabinoid and/or the terpene from seed or plant material as described herein.

Various aspects of the disclosure relate to a method of producing an extract comprising a cannabinoid and/or a terpene. The method comprising extracting the cannabinoid and/or the terpene from a plant or plant cell, or dried flower, as described herein.

Various aspects of the disclosure relate to a method of producing a concentrate comprising a cannabinoid and/or a terpene, The method comprises extracting a concentrate comprising the cannabinoid and/or the terpene from seed or plant material as described herein.

Various aspects of the disclosure relate to a method of producing a concentrate comprising a cannabinoid and/or a terpene. The method comprises extracting a concentrate comprising the cannabinoid and/or the terpene from a plant or plant cell, or dried flower, as described herein.

Various aspects of the disclosure relate to a method of producing an isolate comprising a cannabinoid and/or a terpene. The method comprises isolating the cannabinoid and/or the terpene from seed or plant material as described herein.

Various aspects of the disclosure relate to a method of producing an isolate comprising a cannabinoid and/or a terpene. The method comprises isolating the cannabinoid and/or the terpene from a plant or plant cell, or dried flower, as described herein.

Other aspects and features of the present invention will become apparent to those ordinarily skilled in the art upon review of the following description of specific embodiments of the invention

BRIEF DESCRIPTION OF THE TABLES

Table 1 provides example genomic-based context sequences (SEQ ID NOS:5-14) that contain polymorphic sites within a 20 megabase region within the chromosome identified by GenBank Sequence as CM010796.2 and located between 40,320,373 bases to 59,999,986 bases, and extensive polymorphism information that includes observed alleles and information about the type of polymorphism. The precise positions of the polymorphisms are indicated in bold and underlined type.

Table 2 provides example genomic-based context sequences (SEQ ID NOS:15-24) that contain polymorphic sites within approximately 10 kbp upstream and downstream of the *Cannabis* UPF2 gene, and extensive polymorphism information that includes observed alleles and information about the type of polymorphism. The precise positions of the polymorphisms are indicated in bold and underlined type.

Table 3 provides example genomic-based context sequences (SEQ ID NOS:25-34) that contain polymorphic sites associated with the day length neutral ("autoflowering") phenotype located within approximately 500 kbp upstream and 500 kbp downstream of the *Cannabis* UPF2 gene, and extensive polymorphism information that includes observed alleles and information about the type of polymorphism. The precise positions of the polymorphisms are indicated in bold and underlined type.

Table 4 provides example genomic-based context sequences (SEQ ID NOS:35-44) that contain polymorphic sites associated with the day length neutral ("autoflowering") phenotype located on the chromosome identified by GenBank Sequence as CM010796.2 of the *Cannabis* genome, and polymorphism information that includes observed alleles and information about the type of polymorphism. The precise positions of the polymorphisms are indicated in bold and underlined type.

Definitions

"*Cannabis*" as used herein is inclusive of all species and varieties falling within the genus *Cannabis*, whether *Cannabis sativa*, *Cannabis indica*, or *Cannabis ruderalis*; *C. ruderalis*, and whether or not the variety is "drug" (i.e. contains appreciable levels of the psychoactive cannabinoid tetrahydrocannabinol ("THC")) or "non-drug" (e.g. "hemp").

"Photoperiod" as used herein refers to the day length to which a plant is exposed. Many flowering plants, including *Cannabis*, sense seasonal changes in day length, i.e. photoperiod, which they may take as a signal to flower. For example, most *Cannabis* varieties in cultivation initiate flowering upon a transition from long days (long day length) to short days (short day length). The skilled person understands that the specific length of the "long days" or the "short days" is not crucial. Rather t is the change in the day length that is important to the initiation of flowering.

An "autoflowering phenotype" or "day length neutral phenotype" as used herein describes *Cannabis* plants that initiate flowering with developmental age regardless of the photoperiod (or change therein) to which the plants are exposed.

A "photoperiod phenotype" or "day length sensitive phenotype" as used herein describes *Cannabis* plants that initiate flowering with the onset of decreasing day length (i.e. reduced photoperiod).

"Long days" as used herein refers to day lengths of between about 16 h and about 18 h (i.e. between 6 h and 8 h of darkness).

"Short days" as used herein refers to day lengths of about 12 h (i.e. about 12 of darkness).

"Genetic material" as used herein includes any nucleic add, but particularly deoxyribonucleic acid (DNA) in double-stranded form.

A "polymorphic site" or "polymorphism" as used herein refers to a position within a given genomic region at which variation exists within a population. A polymorphic site" or "polymorphism" is the occurrence of two or more forms (alleles) at a position in the genome within a population, in such frequencies that the presence of the rarest of the forms cannot be explained by mutation alone. Polymorphic sites have at least two alleles, each occurring at a frequency of greater than 1%. Polymorphic sites may occur in both coding regions and noncoding regions of genes or in intergenic regions. Polymorphic sites may involve a single nucleotide polymorphism (i.e. a SNP), or may involve an insertion or deletion ("indel"), or rearrangement.

A "single nucleotide polymorphism" ("SNP") as used herein refers to a polymorphism that involves a variation at a single nucleotide position, whether it be an insertion, a deletion, or a substitution.

A "causative polymorphism" as used herein refers to a variation at a polymorphic site that produces an alteration in the expression of a gene product (whether at the transcriptional, translational, or protein product level) to result in or contribute to a relevant phenotype. Thus, a causative polymorphism is the most predictive of a phenotype.

"Causative" as used herein means resulting in or contributing to a relevant phenotype.

"Linkage" as used herein refers to the co-inheritance of alleles at two or more genes or sequences due to the proximity of the genes on the same chromosome.

"Linkage disequilibrium" ("LD") as used herein refers to any deviation from the expected frequency, i.e. if they were segregating completely independently, of the alleles of two genes in a population. LD is defined in the context of the relative frequency of gamete types in a population of many individuals in a single generation, and is discussed extensively, for example, in WO2009/123396. Loci that have a high degree of LD with an allele of interest are potentially useful in predicting the presence of the allele of interest (i.e. associated with the condition or side effect of interest). Accordingly, two polymorphisms that have a high degree of LD may be equally useful in determining the identity of the allele of interest. Accordingly, the determination of the allele at a polymorphic site can provide the identity of the allele at any polymorphic site in LD therewith. The higher the degree of LD, the more likely that two polymorphisms may reliably function as surrogates for each other. LD may be useful for genotype-phenotype association studies. Until the mechanism underlying the genetic contribution of the day length neutral phenotype is fully understood, LD can be helpful in identifying potential candidate causative variations and in identifying a range of polymorphisms that may be commercially useful for predicting the day length neutral phenotype of a variety.

"Haplotype" as used herein refers to a set of alleles of closely linked loci on a chromosome that tend to be inherited together. Haplotypes along a given segment of a chromosome are generally transmitted to progeny together unless there has been a recombination event. In the absence of a recombination event, haplotypes can be treated as alleles at a single highly polymorphic site for mapping.

The term "traditional breeding techniques" as used herein includes crossing, selfing, selection, backcrossing, marker assisted breeding/selection, mutation breeding etc. as known to the breeder (i.e. methods other than genetic modification/transformation/transgenic methods), by which, for example, a genetically heritable trait can be transferred from one *Cannabis* line or variety to another.

"Backcrossing" as used herein is a traditional breeding technique used to introduce a trait into a plant line or variety. A first parent containing a trait of interest is crossed to a second parent to produce progeny plants. Progeny plants which have the trait are then "backcrossed" to one or the other parent, usually the second parent. After several generations of backcrossing and/or selfing, the progeny typically have the genotype of the second parent but with the trait of interest from the first parent.

"Concentrate" as used herein refer to a product derived from *Cannabis* flowers, whereby excess plant material and other impurities have been removed to leave primarily the cannabinoids and/or terpenes.

"Plant material" as used herein refers to any portion or combination of portions of a *Cannabis* plant including but not limited to seeds, stems, stalks, leaves, flowers, roots, whether fresh or dry, or whether intact, cut, or comminuted. A "field" or a "crop" of plants as used herein refers to a plurality of *Cannabis* plants cultivated together in close proximity.

An "endogenous" gene as referred to herein refers to a gene that is naturally present in a population of *Cannabis* plants and has not been introduced through genetic modification. An "endogenous" gene may be distinguished from a second copy of the gene that is introduced by, for example, genetic modification, and exists at a separate locus in the genome. For the purposes of this disclosure, unless context dictates otherwise, the terms "endogenous UPF2 gene", "*Cannabis* UPF2 gene", and "UPF2 gene" are used interchangeably and the terms "endogenous gene" and "*Cannabis* gene" are used interchangeably A "genetic modification" as used herein broadly refers to any novel combination of genetic material obtained with techniques of modern biotechnology. Genetic modifications include, but are not limited to, "transgenes" in which the genetic material has been altered by the insertion of exogenous genetic material. However, genetic modifications also include alterations (e.g. insertions, deletions, or substitutions) in endogenous genes introduced in a targeted manner with techniques such as CRISPR/Cas9, TALENS, etc. as discussed elsewhere herein. However, for the purposes of this disclosure "genetic modification" is not intended to include novel combinations of genetic material resulting from mutations generated by traditional means of random mutagenesis following by traditional means of breeding. Genetic modifications may be transient or stably inherited.

A "genetically modified" plant or plant cell as used herein broadly refers to any plant or plant cell that possesses a genetic modification as defined herein.

"Nucleotide sequence", "polynucleotide sequence", "nucleic acid" or "nucleic acid molecule" as used herein refers to a DNA or RNA polymer which can be single or double stranded and optionally contains synthetic, non-natural or altered nucleotide bases capable of incorporation into the DNA or RNA polymer. For example, a "fragment" as used herein with respect to the UPF2 gene sequence refers to a portion of the UPF2 gene sequence that is less than the complete sequence. In various embodiments, the fragment comprises at least 20, at least 40, at least 60, at least 80, at least 100, at least 150, at least 200, at least 250, at least 300, at least 350, at least 400, at least 450 or at least 500 contiguous nucleotides.

"Allele" or "variant" as used herein refers to a nucleotide sequence at a polymorphic site where at least two nucleotide sequences exist at the polymorphic site in a population at appreciable frequencies.

A "non-natural variant" as used herein refers to nucleic acid sequences native to an organism but comprising modifications to one or more of its nucleotides introduced by mutagenesis (including point mutations, insertions, and deletions).

"Identity" as used herein refers to sequence similarity between two polynucleotide molecules. Identity can be determined by comparing each position in the aligned sequences. A degree of identity between nucleic acid sequences is a function of the number of identical or matching amino acids or nucleic acids at positions shared by the sequences over a specified region.

"Heterologous" or "exogenous" as used herein refers to DNA that does not occur naturally as part of the plant's genome, or is not normally found in the host genome in an identical context.

"Transgene" as used herein_refers to a segment of DNA containing a gene sequence that has been isolated from one organism and introduced into a different organism. In the context of the present disclosure, the nucleic acid molecules may comprise nucleic acid that is heterologous to the plant in which gene expression (for example, without limitation, UPF2 gene expression) is reduced.

"Expression" or "expressing" as used herein refers to the process by which information from a gene is used in the synthesis of a functional gene product, and may relate to production of any detectable level of a product, or activity of a product, encoded by a gene. Gene expression may be modulated (i.e. initiated, increased, decreased, terminated, maintained or precluded) at many levels including transcription, RNA processing, translation, post-translational modification, protein degradation. In the context of the present disclosure, reduced expression of an endogenous *Cannabis* gene (for example, without limitation, the endogenous UPF2 gene) can be effected by reduced transcription of the endogenous *Cannabis* gene (for example, without limitation, the endogenous UPF2 gene), by reduced translation of mRNA transcripts (for example, without limitation, UPF2 mRNA transcripts), or by the introduction of mutations that either prevent the translation of functional polypeptides or result in the translation of polypeptides with reduced abilities to convert substrate. Such reduced expression of a endogenous *Cannabis* gene (for example, without limitation, the endogenous UPF2 gene) may result from expression of transgenes comprising expression constructs designed to reduce expression of the endogenous genes.

"Decreasing expression", "decreasing activity", "reducing expression", and "reducing activity" as used herein are intended to encompass well known equivalent terms regarding expression and activity such as "inhibiting", "down-regulating", "knocking out", "silencing", etc.

"Expression construct" as used herein refers to any type of genetic construct containing a nucleic acid coding for a gene product in which part or all the nucleic acid encoding sequence is capable of being transcribed. The transcript may be translated into a protein, but it need not be. An expression construct of the disclosure nucleic acid molecule may further comprise a promoter and other regulatory elements, for example, an enhancer, a silencer, a polyadenylation site, a transcription terminator, a selectable marker or a screenable marker.

"Promoter" as used herein refers to a nucleotide sequence that directs the initiation and rate of transcription of a coding sequence. The skilled person will understand that it would be important to use a promoter that effectively directs the expression of the construct in the tissue in which a *Cannabis* gene (for example, without limitation, the UPF2 gene) is usually expressed. For example, the endogenous UPF2 gene promoters could be used. Alternatively, constitutive, tissue-specific, or inducible promoters useful under the appropriate conditions to direct high-level expression of the introduced expression construct could be used.

"Constitutive promoter" as used herein refers to a promoter which drives the expression of the downstream-located coding region in all or nearly all tissues regardless of environmental or developmental factors.

DETAILED DESCRIPTION

Initiation of Flowering in Response to Day Length

Many *Cannabis* varieties in production today have a day length sensitive phenotype. Photoperiod sensitivity is especially limiting for crops grown outdoors at more northern and southern latitudes. Near the equator, the variation of temperature and light (e.g. 12 hours of sun and 12 hours of darkness per day) is minimal, such that the plants do not experience a change in the photoperiod, but they rather flower when the plant reaches maturity. However, at more northerly and southerly latitudes, *Cannabis* is effectively a seasonal plant that needs favourable temperature conditions to grow, and light conditions to flower. Since flowering can be triggered by a change (i.e. a decrease) in day length (i.e. photoperiod), growing conditions when flowering is triggered may be less than optimal for harvest. For example, a sufficient decrease in day length to initiate flowering may not occur until late summer or early fall when frost may occur impacting a plant's quality and/or yield.

In contrast, day length neutral (i.e. "autoflowering") plants can be used at more extreme latitudes since they don't depend on photoperiod to flower. Such plants flower automatically with age, typically have short lifecycles, and, therefore, may mature before the end of the outdoor season yielding a better harvest index. In other words, autoflowering plants can be planted and harvested in a manner that takes advantage of the best growing conditions at such extreme latitudes.

Methods for selecting for day length neutral ("autoflowering") plants are thus needed to develop varieties for more northern/southern latitudes so that plants can be cultivated outdoors and thereby avoid the costs and resources required by indoor cultivation (e.g. in terms of energy consumption, space, and labor that is required for growth in a greenhouse). The suitability of a variety for cultivation in a wide variety of conditions may contribute to high productivity.

Day length neutral phenotypes are also valuable for growth in greenhouses at more extreme latitudes. Shade curtains are required in greenhouses to control the amount of light to which a crop is exposed each day in order to avoid initiation of flowering prematurely, or to simulate a decrease in day length if the initiation of flowering is desired. The cultivation of plants with day length neutral phenotypes avoids the need for such shade curtains.

Thus, breeding *Cannabis* varieties with day length neutral ("autoflowering") phenotypes has significant economic value. Plants with polymorphisms that are predictive of the day length neutral phenotype can be genotyped early in the life of the plant, thereby allowing for the selection of plants desired for further breeding long before the onset for flowering, and for the culling of photoperiod phenotype plants that do not carry the autoflowering trait.

Thus, there is a need for novel genetic markers that are predictive of the day length neutral phenotype. The identification of such genetic markers associated with autoflowering may also reveal novel mutations that are causative of the day length neutral phenotype, and thus identify novel gene targets for the manipulation of response to photoperiod.
Polymorphisms The genomes of all organisms undergo spontaneous mutations in the course of their evolution to generate variant forms of progenitor genetic sequences, whether they be substitutions of one nucleotide for another at the polymorphic site, or insertions or deletions of as few as one nucleotide. In many cases, both progenitor and variant forms survive and co-exist in a species population. The coexistence of multiple forms of a genetic sequence segregating at appreciable frequencies is defined as a "genetic polymorphism" at a "polymorphic site", which includes single nucleotide polymorphisms ("SNPs"), i.e. single base positions in DNA at which different alleles, or alternative nucleotides, exist in a population.

Polymorphic sites may have several alleles. However, the vast majority of polymorphic sites are bi-allelic.

Regardless of whether the polymorphism involves a SNP, an insertion, or a deletion, the polymorphic site is usually preceded and followed by highly conserved "context"

sequences (e.g., sequences that vary in less than 1/100 or 1/1000 members of the populations). An individual may be homozygous or heterozygous for an allele at each polymorphic site.

Causative polymorphisms may typically be positioned within genes encoding a polypeptide product, for example, SNPs that result in changes in the amino acid sequence that result in a defective product. However, causative polymorphisms do not necessarily have to occur in coding regions, and can occur in any region that affects the expression of the protein encoded by a gene, whether by transcription or translation.

Some polymorphisms that are not causative polymorphisms nevertheless are in LD with, and therefore segregate with, the phenotype of concern. Thus, such polymorphisms may be commercially useful for predicting the phenotype.

An association study of a polymorphism and a specific phenotype involves determining the presence or frequency of the polymorphic allele in biological samples from individual plants with the phenotype of interest, such as a day length neutral phenotype, and comparing the information to that of controls (e.g. individual plants that have a day length sensitive phenotype).

A polymorphic site may be surveyed in a sample obtained from an individual having a day length neutral phenotype, compared to control (i.e. day length sensitive plant) samples, and selected for its increased (or decreased) prevalence. Once a statistically significant association is established between one or more polymorphisms and the phenotype of interest, e.g. day length neutral, then the genomic region around the polymorphic site(s) can be thoroughly screened to identify the causative polymorphisms or additional polymorphic sites in LD with the identified polymorphic sites.

Polymorphism Analysis

Once an individual plant is identified as a candidate for having an day length neutral phenotype, or being a carrier of a day length neutral allele, then genetic sequence information may be obtained from the plant for the purpose of determining the identity of the alleles at one or more polymorphic sites associated with the day length neutral phenotype. Genetic sequence information may be obtained in numerous different ways and may involve the collection of a biological sample that contains genetic material, particularly, genomic DNA containing the sequence or sequences of interest. Any suitable genomic DNA samples from *Cannabis* may be used, e.g. from seeds, seedlings, tissue cultures or plants of any age, preferably before flowering has been initiated. Many methods are known in the art for collecting biological samples and extracting genetic material from those samples, as surveyed, for example, in WO 2009/124396 and WO2016/197258. As discussed in WO2019/222835, samples may include the leaves of *Cannabis* seedlings or young plants pressed into a paper matrix, such as a paper matrix (e.g. Whatman™ FTA™ cards) comprising a mixture of chemicals that lyse cells and stabilize nucleic acids on contact for long-term storage at room temperature. The ability to use leaf material pressed into a paper matrix is particularly advantageous because the samples are easily collected, stored at room temperature, and shipped in a format that is not subject to the same restrictions as handling of controlled or regulated substances. Alternatively, the samples may comprise purified DNA isolated from fresh or dry *Cannabis* plant material.

Once an individual plant's genomic DNA has been obtained, the identity of the allele at one or more of the polymorphic sites associated with the day length neutral phenotype can be determined using any one of several methods known in the art. A variety of methods for determining the sequence at polymorphic sites are discussed in, for example, WO 2009/124396, WO2011/133418, WO2016/197258, and WO2019/222835.

Detection or determination of a nucleotide identity, or the presence of one or more SNP(s), may be accomplished by any one of a number of methods or assays known in the art. Many methodologies are useful for determining the identify of alleles at polymorphic sites, and can be assigned to one of four broad groups (sequence-specific hybridization, primer extension, oligonucleotide ligation and invasive cleavage). Furthermore, there are numerous methods for detecting the products of each type of reaction (e.g. fluorescence, luminescence, etc.).

In one popular method discussed in WO2019/222835, High Resolution Melt (HRM) analysis may be conducted in the presence of a common intercalating fluorescent dye to determine the identity of the alleles present at a polymorphic site. As double stranded DNA denatures during HRM, the loss in fluorescence from the dye over time provides different denaturation curves depending on which alleles are present at the polymorphic site.

In another favored method, 5' exonuclease activity or TaqMan™ assay (Applied Biosystems) displaces and cleaves the oligonucleotide probes hybridized to a specific target DNA generating to fluorescent signal. The skilled person understands that numerous methods for determining the identity of an allele at a polymorphic site are known in the art. The skilled person understands that the particular method of determining the identity of the allele at the polymorphic site is not important, so long as it may be reliably determined.

Marker Assisted Breeding

Breeding new varieties, lines and hybrids may be achieved using techniques of crossing and selection on a set of parental lines taking advantage of the plant's method of pollination (self-, sib- or cross-pollination). Multiple rounds of crossing and selection may be needed to produce plant varieties with the desired traits. After each round, the breeder selects candidates with the desired traits or markers for the next round of selection.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the allele of the desired trait (e.g. day length neutral phenotype) and against the alleles of the undesired trait (e.g. day length sensitive phenotype). The use of this procedure can reduce the number of back crosses to the desired parent in a backcrossing program.

The skilled person understands that other desired traits (e.g. altered height, early or late maturity, or disease resistance) can be transferred into selected autoflowering lines by cross pollinating plants having a day length neutral (autoflowering) phenotype with a second parent plant having the desired traits, collecting $F_1$ seed, growing a $F_1$ plant which is allowed to self-pollinate and collect the $F_2$ seed. The $F_2$ seed would then be grown, and individual plants that have the day length neutral phenotype could be selected according to the methods herein. The skilled person will be able to backcross the selected individuals to the second parent.

Identification of Polymorphic Sites in the *Cannabis* Genome that are Associated with the Autoflowering ("Day Length Neutral") Phenotype A plurality of $F_1$ populations featuring one parent with a day length neutral (i.e. autoflowering) phenotype and a second parent with a day length sensitive (i.e. photoperiod) phenotype were generated. Photoperiod sensitive plants were treated with silver thiosulfate ("STS"), a suppressor of ethylene production by plants, to induce the formation of male flowers. Pollen from the male flowers of the photoperiod sensitive plants was then used to pollinate five female plants having a day length neutral phenotype.

The resulting populations were grown under long days (photoperiod=16 h to 18 h). Under these long days, all of the $F_1$ individuals remained vegetative, indicating that they were all photoperiod sensitive, and that the autoflowering trait is recessive. The photoperiod was then switched to short days (photoperiod=12 h), under which the $F_1$ individuals initiated flowering. The $F_1$ individuals were treated with STS to induce the production of male flowers, and placed in pollination bags to self-pollinate to produce $F_2$ seed.

Three $F_2$ populations were grown indoors under long days (photoperiod=16 h to 18 h). Three $F_2$ populations were grown outdoors and scored for flowering when day length was approximately 14 h. In each $F_2$ population, 25% of the plants flowered under the long days. That is, the $F_2$ populations segregated 3:1 photoperiod phenotype: day length neutral phenotype (170 individuals being photoperiod sensitive and 61 day length neutral), which indicates that the day length neutral phenotype is a recessive trait and controlled by a single locus.

A Genome-Wide Association Study (GWAS) was performed using 18,106 "genotyping by sequencing" ("GBS") variants in a Mixed Linear Model in TASSEL5 with 278 samples (47 autoflowering, 231 photoperiod). The kinship (K) matrix was generated using centered Identity-By-State (IBS). The first 5 principal components of the genotype data were included in the model to control population structure. For mapping analysis, phenotypes were coded as 1 for day length neutral phenotype samples and 0 for photoperiod phenotype samples. A number of SNPs in the chromosome identified by GenBank Sequence as CM010796.2 ("chromosome CM010796.2") were identified by GWAS analysis as significantly associated with the day length neutral phenotype. Additionally, an association analysis using a General Linear Model was performed using 302,334 whole-genome shotgun variants on chromosome CM010796.2 in TASSEL5 with 39 samples (12 autoflowering, 27 photoperiod). For mapping analysis phenotypes were coded as 1 for day length neutral phenotype samples and 0 for photoperiod phenotype samples. 1,867 variants were found to be significantly correlated with the day length neutral phenotype in a region spanning approximately position 40,320,373 to 59,999980.

To develop a genetic marker to select plants containing the day length neutral phenotype, a genetic map of the region associated with the autoflowering trait in chromosome CM010796.2 was constructed. The genetic map of this region informed the size of the region carrying the autoflowering trait, its recombination rate and the genetic distance between markers. This information was used to select suitable SNP(s) for use in marker assisted selection and to establish a breeding protocol. To construct the genetic map of chromosome CM010796.2, 192 seeds from an $F_2$ population obtained from a single $F_1$ selfed individual from an initial cross between a photoperiod sensitive parent and a day length neutral parent were germinated. The seedlings were genotyped using a custom-made 5KSeqSNP array from LGC™ to assess the recombination rate of chromosome CM010796.2 and to measure the genetic distance between the SNPs identified by the GWAS analysis. The 5KSeqSNP array included some of the polymorphic SNPs in day length neutral plants.

Segregating alleles in the $F_2$ population were used to build a genetic map of chromosome CM010796.2 using a Kosambi map function as implemented in a R-qtl package. SNPs with genotypic data in at least 160 individuals were retained for map construction. A total of 90 SNPs were segregating in chromosome CM010796.2 and allowed the construction of a genetic map with an average genetic distance between markers of 1 centimorgan (cM). The recombination rates were analyzed across chromosome CM010796.2. Two major regions of low recombination were observed. This indicates that, in addition to the centromere's "natural' low recombination zone, there is a distinct region comprising about 20 megabases in one of the chromosome arms of chromosome CM010796.2 that displays very low recombination rates. 24 of the 90 SNPs with very little to no recombination fell within this about 20 megabase region. This about 20 megabase region is located between about megabases to about 60 megabases in chromosome CM010796.2. In some embodiments, this about 20 megabase region is located between about 40,320,373 bases to about 59,999,986 bases. Without being bound by theory, the inventors speculate that the second low recombination region (i.e. the about 20 megabase region in chromosome CM010796.2) may be attributable to the autoflowering trait originating from an ancestral *Cannabis* line, presumably from *Cannabis ruderalis*, which would be divergent enough to disrupt the normal process of cross-over and recombination. Thus, the autoflowering trait (i.e. the day length neutral phenotype) is attributed to the low recombination region comprising about 20 megabases (i.e. the "about 20 megabase region").

In some embodiments, the low recombination region in chromosome CM010796.2 that may be attributable to the autoflowering trait is about 1 megabase, about 2.5 megabases, about 5 megabases, about 7.5 megabases, about 10 megabases, about 12.5 megabases, about 15 megabases, about 17.5 megabases or about 20 megabases located between about 40 megabases to about 60 megabases. In some embodiments, the low recombination region is located within a region in *Cannabis* chromosome CM010796.2 selected from: about 40 megabases to about 42.5 megabases, about 40 megabases to about 45 megabases, about 40 megabases to about 50 megabases, about 42.5 megabases to about 45 megabases, about 42.5 megabases to about 47.5 megabases, about 42.5 megabases to about 50 megabases, about 42.5 megabases to about 52.5 megabases, about 45 megabases to about 47.5 megabases, about 45 megabases to about 50 megabases, about 45 megabases to about 52.5 megabases, about 45 megabases to about 55 megabases, about 47.5 megabases to about 50 megabases, about 47.5 megabases to about 52.5 megabases, about 47.5 megabases to about 55 megabases, about 47.5 megabases to about 57.5 megabases, about 50 megabases to about 52.5 megabases, about 50 megabases to about 55 megabases, about 50 megabases to about 57.5 megabases, about 50 megabases to about 60 megabases, about 52.5 megabases to about 55 megabases, about 52.5 megabases to about 57.5 megabases, about 52.5 megabases to about 60 megabases, about 55 megabases to about 57.5 megabases, about 55 megabases to about 60 megabases, or about 57.5 megabases and about 60 megabases.

Due to the low recombination of the about 20 megabase region in chromosome CM010796.2, one or more polymorphism in that region (or in any one or more of the 1,172 genes within this region) in the *Cannabis* genome may be causative of and/or contribute to the day length neutral phenotype. Thus, any polymorphism in this low recombination region would be in strong linkage disequilibruim with the causative gene(s) and could be used as a marker to select individuals with the day length neutral phenotype in a segregating population.

For example, about 1,867 variants have been identified in the about 20 megabase region in chromosome CM010796.2. Any one or more of these variants may be causative of the day length neutral phenotype and/or in strong linkage disequilibrium with the causative gene(s) and could be used as a marker to select individuals with the day length neutral phenotype.

Example polymorphic sites associated with the day length neutral phenotype, and within the about 20 megabase region (i.e. between about 40 megabases and about 60 megabases in chromosome CM010796.2), and the alleles present at these sites, are presented in Table 1. The skilled person understands that additional polymorphic sites not identified in Table 1 but that are within the about 20 megabase region, and the alleles present at these sites, may be used for the identification of plants that have the day length neutral phenotype or that are carriers of the trait for day length neutral phenotype.

A putative SNP in the *Cannabis* UPF2 gene was found across different genome assemblies (Laverty and DT2 improved) from "genotyping by sequencing" ("GBS") data. To validate this putative SNP, the following primers around the putative SNP were designed: SW23 (CTAAAAAAAGTAGCGCTTCGGG; SEQ ID NO: 45) and SW28 (TGTAGCCGTGGGGCAACTAAAACG; SEQ ID NO: 46). PCR amplification of selected $F_2$ plants (7 autoflowering, 9 photoperiod) was performed using the primers. 1 ul DNA was amplified with 1 uM of each primer, 0.2 mM dNTP, 3 mM $MgCl_2$ and 2 Units Taq polymerase, using the following cycling program: 5 min at 98° C., then 30 cycles of 10 sat 98° C., 30 s at 58° C., 1 min at 72° C. and final extension 10 min at 72° C. Surprisingly, the expected FOR product was absent in all plants having the day length neutral phenotype.

To test if the absence of the FOR product in plants with a day length neutral phenotype was caused by mutations at the primer region, a new set of primers flanking the previous sequences were designed as SW36 (GTACAGTAAAC-TATCTCAATTTCT; SEQ 10 NO: 3) and SW37 (AC-CACACCTTTTCCAATTGGACTC; SEQ ID NO: 4). By employing the same method as above, FOR products were detected using the new pair of primers in autoflowering samples. The SW28 primer sequence was absent in the PCR products, which indicates that plants having the day length neutral phenotype have a deletion at this polymorphic site. More samples (i.e. 8 autoflowering, 11 photoperiod) were tested, and validated the result.

Upon further investigation, this deletion was determined to be located in the 3' UTR of the *Cannabis* UPF2 gene and comprise the sequence of SEQ ID NO: 2 (i.e. SEQ ID NO: 2 is missing from both copies of the UPF2 gene in plants displaying a day length neutral phenotype). While not conclusive, the data indicates that the deletion of this DNA fragment is an important determinant, and may be causative, of the day length neutral phenotype.

The *Cannabis* UPF2 gene encodes a nonsense-mediated mRNA decay (NMD) factor protein. NMD is an important mRNA quality surveillance pathway in all eukaryotes that eliminates aberrant mRNAs. In *Arabidopsis*, silencing the UPF2 gene results in aberrant stress responses under long (16 h) days, but has a lesser effect under short days. As such, it appears that UPF2 may play a role in mediating the response to long days (i.e. 16 h) in *Arabidopsis*. Accordingly, it is reasonable to expect that UPF2 may play a role in mediating inhibition of flowering in response to long days (16 to 18 h) in *Cannabis*.

However, UPF2 is within an about 20 megabase region containing 1,172 genes and numerous mutations, any of which could be the causative allele responsible for the day length neutral phenotype. For example, UPF2 is within an about 1 megabase region (located between about 41,177,432 bases and about 42,183,459 bases in chromosome CM010796.2) containing 46 additional genes and numerous mutations, any of which could be the causative allele responsible for the day length neutral phenotype.

Moreover, once the allele of the *Cannabis* gene within the about 20 megabase region is established as associated with the day length neutral phenotype, the skilled person understands that any allele at additional polymorphic sites on the chromosome that is in linkage disequilibrium with this allele will also be associated with the day length neutral phenotype. For example, once the allele of the UPF2 gene from which SEQ ID NO: 2 is deleted is established as associated with the day length neutral phenotype, the skilled person understands that any allele at additional polymorphic sites on the chromosome that is in linkage disequilibrium with this allele of UPF2 will also be associated with the day length neutral phenotype.

Accordingly, GWAS and GBS allowed for the identification of more polymorphic sites that are in linkage disequilibrium with the deletion of SEQ ID NO: 2 from the UPF2 gene. Example polymorphic sites within 10 kbp upstream and downstream of the UPF2 gene, and the alleles present at these sites, are presented in Table 2. Additional example polymorphic sites associated with the day length neutral phenotype and within 500 kbp upstream and 500 kbp downstream of the UPF2 gene, and the alleles present at these sites, are presented in Table 3. Further example polymorphic sites on chromosome CM010796.2 that are significantly associated with the day length neutral phenotype are presented in Table 4. The skilled person understands that it may be possible to use any one of these polymorphisms as a surrogate marker for the deletion in the UPF2 gene for the identification of plants that have the day length neutral phenotype or that are carriers of the trait for the day length neutral phenotype. The skilled person also understands that additional polymorphic sites not identified in any of Tables 2, 3 or 4 but that are within 3,000 bp upstream and 3,000 bp downstream of the UPF2 gene, and the alleles present at these sites, may be used for the identification of plants that have the day length neutral phenotype or that are carriers of the trait for day length neutral phenotype.

Identification of Plants that have an Autoflowering ("Day Length Neutral") Phenotype Thus, the skilled person understands that the polymorphisms disclosed in Tables 1, 2, 3, and 4 are useful in methods of identifying whether or not a *Cannabis* plant has a day length neutral phenotype, or is a carrier of a trait for a day length neutral phenotype, but that other polymorphisms within the about 20 megabase region may be useful in such methods.

In one aspect, this disclosure provides a method comprising testing nucleic acid from a *Cannabis* plant to determine the presence or absence a polymorphic site in an about 20 megabase region (or in any one or more of the 1,172 endogenous genes in that region) in chromosome CM010796.2 located between about 40 megabases and about 60 megabases. For example, the disclosure provides a method comprising testing nucleic acid from a *Cannabis* plant to determine the presence or absence of a deletion in the 3' untranslated region of the endogenous UPF2 gene comprising a portion (i.e. all or a part) of SEQ ID NO: 2. In particular, the methods are for identifying whether or not the *Cannabis* plant has a day length neutral phenotype, or is a carrier of a trait for a day length neutral phenotype. The presence of a variation indicates that the plant has a day length neutral phenotype or is a carrier of the trait for the day length neutral phenotype. In some embodiments, testing nucleic acid from the *Cannabis* plant to determine the presence or absence of the variation comprises testing for the presence or absence of SEQ ID NO: 2 from SEQ ID NO: 15, or a portion thereof wherein the absence of SEQ ID NO: 2 or a portion thereof from SEQ ID NO: 15 in both copies of the UPF2 gene indicates that the plant has a day length neutral phenotype. The absence of SEQ ID NO: 2 or a portion thereof from SEQ ID NO: 15 in only one copy of the UPF2 gene indicates that the plant is a carrier of the trait for a day length neutral phenotype.

However, the skilled person understands that if the UPF2 allele comprising the deletion of SEQ ID NO: 2 is causative of the day length neutral phenotype, i.e. if the day length neutral phenotype results from a loss or gain of UPF2 gene expression/activity, then any loss or gain of function of the UPF2 gene could function as a marker of the day length neutral phenotype. If the presence or absence of an allele at a polymorphic site within the about 20 megabase region (or within any one or more of the 1,172 endogenous genes in the region) is causative of the day length neutral phenotype, i.e. if the day length neutral phenotype results from a loss or gain of any one or more of the 1,172 endogenous gene expression/activity, then any loss or gain of function of such gene could function as a marker of the day length neutral phenotype. The skilled person would also recognize that any SNPs in close proximity to a causative gene (i.e. within about 3,000 bases of the 5' and 3' ends of the gene and/or within the promoter and/or untranslated region flanking the gene) could also function as a marker of the day length neutral phenotype. Thus, in another aspect, this disclosure more generally provides a method comprising testing nucleic acid from a *Cannabis* plant to determine the presence or absence of an allele at a polymorphic site in the about 20 megabase region (or in any one or more of the 1,172 endogenous genes within the region). For example, another aspect of the disclosure generally provides a method comprising testing nucleic acid from a *Cannabis* plant to determine the presence or absence of a variation in the endogenous UPF2 gene. The methods are for identifying whether or not the *Cannabis* plant has a day length neutral phenotype, or is a carrier of a trait for a day length neutral phenotype. The presence of the allele at a polymorphic site or variation indicates that the plant has a day length neutral phenotype or is a carrier of the trait for the day length neutral phenotype. The variation may be a loss of function mutation or a gain of function mutation in any one or more of the 1,172 endogenous genes in the about 20 megabase region (for example, without limitation, a loss of function mutation or a gain of function mutation in the UPF2 gene), which may be a point mutation (e.g. a substitution, a missense mutation or a nonsense mutation), a deletion, or an insertion. The presence of the variation in both copies of the endogenous gene (for example, without limitation, in both copies of the endogenous UPF2 gene) may indicate that the plant has a day length neutral phenotype. The presence of the variation in only a single copy of the endogenous gene (for example, without limitation, the endogenous UPF2 gene) may indicate that the plant is a carrier of the trait for the day length neutral phenotype.

The skilled person further understands that any polymorphism in linkage disequilibrium with an allele at a polymorphic site of the about 20 megabase region can be used as a surrogate marker for the day length neutral phenotype. For example, any polymorphism in linkage disequilibrium with the allele of the UPF2 gene with the deletion in the 3' untranslated region (i.e. the deletion of SEQ ID NO: 2) can be used as a surrogate marker for the day length neutral phenotype. Thus, in another aspect, this disclosure provides a method comprising testing nucleic acid from a *Cannabis* plant to determine the presence or absence of one or more variation (i.e. allele at a polymorphic site) that is in linkage disequilibrium (i.e. where the coefficient of correlation of the alleles, $r^2$, is 0.9 to 1) with a variation in the about 20 megabase region (for example, without limitation, with the UPF2 allele comprising the deletion of SEQ ID NO: 2). The method is for identifying whether a *Cannabis* plant has a day length neutral phenotype, or is a carrier of a trait for a day length neutral phenotype. The presence of the variation indicates that the plant has a day length neutral phenotype or is a carrier of the trait for the day length neutral phenotype. The presence of the allele indicates that the plant has a day length neutral phenotype or is a carrier of the trait for the day length neutral phenotype.

Again, the skilled person understands that if this deletion of SEQ ID NO: 2 is causative of the day length neutral phenotype, then the presence or absence of one or more variation (i.e. allele at a polymorphic site) that is in linkage disequilibrium (i.e. $r^2$=0.9 to 1) with any loss or gain of function variation in the endogenous UPF2 gene could be used as a marker for the day length neutral phenotype.

Example polymorphisms in linkage disequilibrium with any one or more of the 1,172 genes within the about 20 megabase region in chromosome CM010796.2 (i.e. between about 40 megabases and about 60 megabases), and which are associated with the day length neutral phenotype, are disclosed in Table 1. The skilled person understands that additional polymorphic sites not identified in Table 1 but that are within the about 20 megabase region, and the alleles present at these sites, may be used for the identification of plants that have the day length neutral phenotype or that are carriers of the trait for day length neutral phenotype. Thus, a further aspect of this disclosure is a method comprising testing nucleic acid from a *Cannabis* plant to determine the presence or absence of an allele at a polymorphic site as indicated, for example, for any one or more of the nucleotide sequences identified in Table 1. Again, the method is for identifying whether a *Cannabis* plant has a day length neutral phenotype, or is a carrier of a trait for a day length neutral phenotype. The presence of the allele indicates that the plant has a day length neutral phenotype or is a carrier of the trait for the day length neutral phenotype.

Example polymorphisms in linkage disequilibrium with the UPF2 allele comprising the deletion of SEQ ID NO: 2, and which are associated with the day length neutral phenotype, are disclosed in Tables 2, 3, and 4. The skilled person understands that additional polymorphic sites not identified in any of Tables 2, 3 or 4 but that are within approximately 3,000 bp upstream and 3,000 bp downstream of the *Cannabis* UPF2 gene, and the alleles present at these sites, may be used for the identification of plants that have the day length neutral phenotype or that are carriers of the trait for day length neutral phenotype. Thus, a further aspect of this disclosure is a method comprising testing nucleic acid from a *Cannabis* plant to determine the presence or absence of an allele at a polymorphic site as indicated, for example, for any one or more of the nucleotide sequences identified in Table 2, 3, or 4. Again, the method is for identifying whether a *Cannabis* plant has a day length neutral phenotype, or is a carrier of a trait for a day length neutral phenotype. The presence of the allele indicates that the plant has a day length neutral phenotype or is a carrier of the trait for the day length neutral phenotype.

The skilled person further understands that any polymorphic site that itself is in linkage disequilibrium with one or more of the example polymorphisms identified in Tables 1, 2, 3, and 4 that is associated with the day length neutral phenotype can also be used as marker for the day length neutral phenotype. Thus, a further aspect of this disclosure relates to a method comprising testing nucleic acid from a *Cannabis* plant to determine the presence or absence of a first allele that is in linkage disequilibrium $r^2=0.9$ to 1 with a second allele at a polymorphic site as indicated for any one or more of the example nucleotide sequences identified in Table 1, 2, 3 or 4. The method is for identifying whether a *Cannabis* plant has a day length neutral phenotype, or is a carrier of a trait for a day length neutral phenotype. The presence of the second allele indicates that the plant has a day length neutral phenotype or is a carrier of the trait for the day length neutral phenotype, such that the presence of the first allele indicates that the plant has a day length neutral phenotype or is a carrier of the trait for the day length neutral phenotype.

In various embodiments of the methods described above, "testing" comprises nucleic acid amplification, e.g. amplification carried out by polymerase chain reaction (PCR).

The skilled person understands that testing may also involve sequencing, 5' nuclease digestion, molecular beacon assay, oligonucleotide ligation assay, size analysis, single-stranded conformation polymorphism analysis, denaturing gradient gel electrophoresis (DGGE), or any other appropriate methodology as described elsewhere herein and in references cited herein.

In preferred embodiments, testing is performed using an allele-specific method, e.g. allele-specific probe hybridization, allele-specific primer extension, or allele-specific amplification. Testing may be carried out using an allele-specific primer that comprises a sequence selected from the group consisting of SEQ ID NOS: 3, 4 and sequences fully complementary thereto.

Marker-Assisted Breeding

The skilled person further understands that the methods for identifying plants that have a day length neutral phenotype, or are a carrier of the trait, are particularly useful in methods of marker-assisted breeding to efficiently introduce the day length neutral trait into *Cannabis* varieties having desirable traits but a photoperiod phenotype.

Thus, another aspect of the disclosure relates to methods of producing a *Cannabis* plant with a day length neutral phenotype. The method comprises initially performing a first cross of a first parent having at least one allele associated with a day length neutral phenotype at a polymorphic site as indicated for any one of the example nucleotide sequences identified in Table 1, 2, 3, or 4 with a second parent that has a day length sensitive phenotype. The skilled person understands that it is not necessary that the first parent have the day length sensitive phenotype so long as the first parent is at least a carrier of the trait, such that the methods described above can be used to screen progeny of the cross for the presence of the allele associated with the day length neutral phenotype. The method further comprises identifying a first progeny plant from the first cross that has a day length neutral phenotype, or that is a carrier of a trait for a day length neutral phenotype, according to a method as described above under the section entitled "Identification of Plants that have an Autoflowering ("Day Length Neutral") Phenotype".

After a first progeny plant that is a carrier of a trait for a day length neutral phenotype is identified, then the first progeny plant may be self-pollinated to produce $F_2$ progeny. The method may then further include identifying an $F_2$ progeny plant that has a day length neutral phenotype according to the method described above. However, the skilled person would understand that 25% of the resulting $F_2$ progeny should have the day length neutral phenotype, such that the skilled person may choose not to screen for plants carrying two copies of the allele associated with the day length neutral phenotype. Alternatively, the skilled person may be interested in selecting $F_2$ progeny that are carriers of the trait and thus may choose an $F_2$ progeny plant that is a carrier of the trait for the day length neutral phenotype according to the method described above.

Alternatively, after a first progeny plant that is a carrier of a trait for a day length neutral phenotype is identified, the method may comprise backcrossing the first progeny plant to the first parent, and then identifying a progeny plant from the backcross that has a day length neutral phenotype according to a method described above. Such strategy may be of interest where the interest is in introducing a particular trait from the photoperiod sensitive variety to the variety with the day length neutral phenotype.

Alternatively, the method may comprise backcrossing the first progeny plant to the second parent, and then identifying a progeny plant from the backcross that is a carrier of the trait for the day length neutral phenotype according to the method as described above. Such strategy may be useful after a first progeny plant that is a carrier of a trait for a day length neutral phenotype is identified where the goal is to introduce only the autoflowering trait to the variety of the second parent.

In another embodiment, after a first progeny plant that is a carrier of a trait for a day length neutral phenotype is identified, the method further comprises performing a second cross of the first progeny plant with a second progeny plant identified as a carrier of a trait for a day length neutral phenotype according to a method as described above. The method then comprises identifying a progeny plant from the second cross that has a day length neutral phenotype, or is a carrier of the trait, according to a method as described above.

In another aspect, the disclosure provides methods of producing a *Cannabis* plant with a day length neutral phenotype comprising initially performing a first cross of a first parent that has a day length neutral phenotype and is homozygous for at least one allele associated with a day length neutral phenotype at a polymorphic site as indicated for any one of the example nucleotide sequences identified in Table 1, 2, 3 or 4, with a second parent that has a day length sensitive phenotype to produce $F_1$ progeny. The skilled person understands that each of the $F_1$ progeny will be a carrier of the trait for the day length neutral phenotype such that it is not necessary to screen for a carrier using any of the methods described above. Rather, the method further comprises selfing the $F_1$ progeny to produce $F_2$ progeny and then identifying an $F_2$ progeny plant that has a day length neutral phenotype, or that is a carrier of a trait for a day length neutral phenotype, according to a method as described above.

In yet another aspect, the disclosure provides methods of producing a *Cannabis* plant with a day length neutral phenotype comprising initially identifying a first parent homozygous for at least one allele associated with a day length neutral phenotype at a polymorphic site as indicated for any one of the example nucleotide sequences identified in Table 1, 2, 3 or 4 according to a method described above. The method further comprises crossing the first parent to a second parent that has a day length sensitive phenotype to produce $F_1$ progeny. Again, the skilled person understands that each of the $F_1$ progeny will be a carrier of the trait for the day length neutral phenotype such that it is not necessary to screen for a carrier using any of the methods described above. The method thus further comprises selfing the $F_1$ progeny to produce $F_2$ progeny, and identifying an $F_2$ progeny plant that has a day length neutral phenotype. While it is not necessary to screen the $F_2$ progeny according to the methods described above to determine whether or not a plant has a day length neutral phenotype (i.e. because 25% of the plants should have a day length neutral phenotype), the skilled person could do so if it were desirable to know the phenotype before flowering is initiated. Alternatively, the skilled person may want to screen the $F_2$ progeny for carriers of the trait.

The skilled person also understands that there may be many reasons as to why it may be beneficial to maintain lines that are heterozygous for the trait that causes the day length neutral phenotype. First, the phenotype is not completely recessive, such that plants heterozygous for the allele are somewhat sensitive to day length and thus initiate flowering later than plants having the day length neutral phenotype when grown under long days. Thus, there may be situations where it would be advantageous to select for and cultivate plants that had such an intermediate phenotype. Second, vegetative propagation of plants having a day length neutral phenotype may induce flowering. Accordingly, it may be advantageous in some circumstances to maintain the autoflowering trait in heterozygous plants and then perform the cross (or self-pollinate) to produce plants having the day length neutral phenotype when it is desired.

Presuming that the deletion of SEQ ID NO: 2 from the UPF2 gene is causative of the day length neutral phenotype, then the skilled person would understand that any plant having a loss or gain of function mutation in the UPF2 gene could be used in breeding programs to introduce the day length neutral phenotype into a day length sensitive variety. Presuming that a deletion from any one or more of the 1,172 genes within the about 20 megabase region is causative of the day length neutral phenotype, then the skilled person would understand that any plant having a loss or gain of function mutation in such gene(s) could be used in breeding programs to introduce the day length neutral phenotype into a day length sensitive variety. Thus, further aspects of the disclosure pertain to methods of producing a *Cannabis* plant with a day length neutral phenotype comprising initially performing a first cross of a first parent identified as having at least one loss of function mutation allele and/or at least one gain or function allele of any one or more of the 1,172 genes within the about 20 megabase region (for example, without limitation, at least one loss of function mutation allele and/or at least one gain of function mutation allele of the UPF2 gene) according to a method as described above with a second parent that has a day length sensitive phenotype. The method further comprises performing a second cross of a first progeny of the first cross with a second progeny of the first cross to produce a plant that is homozygous for the loss or gain of function mutation allele, which plant would have a day length sensitive phenotype.

Polynucleotides and Kits

The skilled person further understands that the disclosure pertains to reagents and kits that are useful or necessary for performing the methods described above for identifying plants that have a day length neutral phenotype or are carriers of the trait for the day length neutral phenotype, and for marker assisted breeding of the day length neutral phenotype.

Thus, the disclosure further pertains to an allele-specific polynucleotide for use in the methods described herein. In some embodiments, the polynucleotide is specific for a variation (e.g. a deletion) in any one or more of the 1,172 endogenous genes within the about 20 megabase region. In particular embodiments, the polynucleotide is specific for the variation in the endogenous UPF2 gene. In particular embodiments, the polynucleotide is specific for the allele of UPF2 comprising the deletion of SEQ ID NO: 2. In particular embodiments, the allele-specific polynucleotide is specific for an allele at a polymorphic site as indicated for any one or more of the example nucleotide sequences identified in Table 1, 2, 3 or 4, or an allele that is in linkage disequilibrium therewith. The allele-specific polynucleotide may be at least 16 nucleotides in length. In various embodiments, the polynucleotide is detectably labeled, e.g. with a fluorescent dye.

The disclosure further pertains to kits for use in the methods described above. The kits comprise at least one allele-specific polynucleotide as described above and at least one further component, e.g. a buffer, deoxynucleotide triphosphates (dNTPs), an amplification primer pair, an enzyme, or any combination thereof. The enzyme may be a polymerase or a ligase.

In certain embodiments, the kits are provided to laboratories, whereby a breeder collects biological samples from individual plants and submits the samples to the laboratory for testing using the kits to determine the genotype at one or more polymorphic sites disclosed herein, and the plant's likelihood of having a day length neutral phenotype, and to provide the results to the breeder e.g. in the form of a report as described below. Alternatively, the kits include reagents for performing the testing of the samples by the breeders themselves.

The Applicant further understands that the methods disclosed herein could be automated and implemented with the use of computers. The results of a test to determine the identify of an allele at a polymorphic site may be presented as a "report", that can be generated as part of a testing process, which can be provided to the breeder or any other intended recipient in physical or electronic form. Reports may include the alleles that the individual plant carries at various polymorphic sites and/or an individual plant's likelihood of having a day length neutral phenotype, or being a carrier of the trait.

Molecular Modification

Presuming that a deletion from any one or more of the 1,172 genes within the about 20 megabase region is causative of the day length neutral phenotype, then the skilled person would understand that a *Cannabis* plant could be genetically modified to decrease expression of UPF2 gene to result in the day length neutral phenotype. For example, presuming that the deletion of SEQ ID NO: 2 from the UPF2 gene is causative of the day length neutral phenotype, then the skilled person would understand that a *Cannabis* plant could be genetically modified to decrease expression of UPF2 gene to result in the day length neutral phenotype.

Accordingly, a further aspect of the disclosure relates to methods for producing a day length neutral *Cannabis* plant comprising decreasing the expression of any one or more of the 1,172 genes within the about 20 megabase region (for example, without limitation, the endogenous UPF2 gene) in the plant. Decreasing the expression of the endogenous gene (s) (for example, without limitation, the endogenous UPF2 gene) may include introducing or producing a loss or gain of function allele in the endogenous gene. The loss or gain of function allele may include a point mutation, an insertion, or a deletion. The point mutation may be a substitution. The point mutation may be a nonsense mutation. An insertion could include a T-DNA or a transposable element. Decreasing the expression of the endogenous gene (s) (for example, without limitation, the endogenous UPF2 gene) may comprise expressing a heterologous nucleic acid molecule homologous to a portion of the endogenous gene, wherein the heterologous nucleic acid molecule decreases expression of the endogenous gene (s) (for example, without limitation, the endogenous UPF2 gene). The heterologous nucleic acid molecule may decrease expression of the gene(s) (for example, without limitation, the UPF2 gene) by RNA interference. In some embodiments, the heterologous nucleic acid molecule may comprise a portion of SEQ ID NO: 1.

A further aspect of the disclosure relates to methods of generating a *Cannabis* plant having a day length neutral phenotype comprising initially using a molecular methodology to identify a first plant as comprising a loss or gain of function allele in any one or more of the 1,172 genes within the about 20 megabase region (for example, without limitation, in the UPF2 gene). The method further comprises performing a first cross of said first plant to a second plant followed by performing a second cross of progeny from the first cross. Prior to performing the second cross, progeny from the first cross may be screened to identify plants comprising the loss or gain of function allele in any one or more of the 1,172 genes within the about 20 megabase region (for example, without limitation, the UPF2 gene) for use in the second cross. The method further comprises screening progeny of the second cross for a plant that is homozygous for the loss or gain of function allele in any one or more of the 1,172 endogenous genes within the about 20 megabase region (for example, without limitation, the endogenous UPF2 gene). The loss or gain of function allele in any one or more of the 1,172 endogenous genes within the about 20 megabase region (for example, without limitation, the endogenous UPF2 gene) may be generated by genetic modification of the first plant or an ancestor thereof. The molecular methodology may include targeting induced local lesions in genomes (TILLING) methodology.

Reduction of Gene Expression

Gene expression and/or activity in genetically modified plants of the present invention may be reduced by any method that results in reduced activity of the corresponding protein in the plant. For example, UPF2 gene expression and/or activity in genetically modified plants of the present invention may be reduced by any method that results in reduced activity of the UPF2 protein in the plant. This may be achieved by e.g. by altering gene activity (for example, without limitation, UPF2 gene activity) at the DNA, mRNA and/or protein levels.

Mutating the Endogenous Genes

In one aspect, the present disclosure relates to genetic modifications targeting one or more of the 1,172 endogenous genes within the about 20 megabase region (for example, without limitation, the UPF2 gene) to alter gene expression and/or activity. The endogenous gene(s) (for example, without limitation, the endogenous UPF2 gene) may be altered by, without limitation, knocking-out the gene(s) (e.g. the UPF2 gene); or knocking-in a heterologous DNA to disrupt the gene(s) (for example, without limitation, the UPF2 gene). The skilled person would understand that these approaches may be applied to the coding sequences, the promoter or other regulatory elements necessary for gene transcription. For example, technologies such as CRISPR/Cas9 and TALENS can be used to introduce loss or gain of function mutations in one or more of the 1,172 endogenous genes within the about 20 megabase region (for example, without limitation, the endogenous UPF2 gene). Plants having at least one mutagenized allele comprising a loss or gain of function mutation can then be self-fertilized to produce progeny homozygous for the loss or gain of function alleles in one or more of the 1,172 genes within the about 20 megabase region (for example, without limitation, the UPF2 gene).

Deletions lack one or more nucleotides of the one or more of the 1,172 genes within the about 20 megabase region (e.g. the endogenous UPF2 gene) or residues of the corresponding endogenous protein (e.g. the UPF2 protein). For the purposes of this disclosure, a deletion variant includes embodiments in which no amino acids of the endogenous protein are translated, e.g. where the initial "start" methionine is substituted or deleted.

Insertional mutations typically involve the addition of material at a non-terminal point in the gene or polypeptide, but may include fusion proteins comprising amino terminal and carboxy terminal additions. Substitutional variants typically involve a substitution of one amino acid for another at one or more sites within the protein.

Expression of Transgenes Targeting the Endogenous Genes

In another aspect, the present disclosure relates to reducing the expression and/or activity of one or more of the 1,172 genes within the about 20 megabase region (e.g. the endogenous UPF2 gene) by targeting its mRNA transcripts. In this regard, levels of corresponding mRNA transcripts (e.g. levels of UPF2 mRNA transcripts) may be reduced by methods known in the art including, but not limited to, co-suppression, antisense expression, short hairpin (shRNA) expression, interfering RNA (RNAi) expression, double stranded (dsRNA) expression, inverted repeat dsRNA expression, micro interfering RNA (miRNA), simultaneous expression of sense and antisense sequences, or a combination thereof. Various such methods are described in WO2018/027324.

In one embodiment, the present disclosure relates to the use of nucleic acid molecules that are complementary, or essentially complementary, to at least a portion of the molecule set forth in SEQ ID NO: 1. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO: 1 under physiological conditions.

The phenomenon of co-suppression in plants relates to the introduction of transgenic copies of a gene resulting in reduced expression of the transgene as well as the endogenous gene. The observed effect depends on sequence identity between the transgene and the endogenous gene.

The term "RNA interference" (RNAi) refers to well-known methods for down regulating or silencing expression of a naturally occurring gene in a host plant. RNAi employs a double-stranded RNA molecule or a short hairpin RNA to change the expression of a nucleic acid sequence with which they share substantial or total homology.

Antisense suppression of gene expression does not involve the catalysis of mRNA degradation, but instead involves single-stranded RNA fragments binding to mRNA and blocking protein translation.

Expression of one or more of the 1,172 genes within the about 20 megabase region (for example, without limitation, expression of the UPF2 gene) may be suppressed using a synthetic gene(s) or an unrelated gene(s) that contains about 21 bp regions or longer of high homology (preferably 100% homology) to the endogenous coding sequences of the gene (for example, without limitation, the UPF2 gene).

Nucleic acid molecules that are substantially identical to portions of one or more of the 1,172 genes within the about 20 megabase region (for example, without limitation, to portion of the UPF2 gene) may also be used in the context of the disclosure. As used herein, one nucleic acid molecule may be "substantially identical" to another if the two molecules have at least 60%, at least 70%, at least 80%, at least 82.5%, at least 85%, at least 87.5%, at least 90%, at least 92.5%, at least 95%, at least 96%, at least 97%, at least 98%, or at least 99% sequence identity. Thus, a nucleic acid sequence comprising a nucleic acid sequence that is at least 60%, at least 65%, at least 70%, at least 75%, at least 80%, at least 85%, at least 90%, at least 92.5%, at least 95%, at least 96%, at least 97%, at least 98% or at least 99% identical to SEQ ID NO: 1 may be suitable for use in the context of this disclosure.

Fragments of nucleic acid sequences of one or more of the 1,172 genes within the about 20 megabase region (for example, without limitation, the UPF2 gene) may be used. Such fragments may have lengths of at least 20, at least 50, at least 100, at least 150, at least 200, at least 250, at least 300, at least 350, at least 400, at least 450 or at least 500 contiguous nucleotides of a nucleic acid sequence of the gene (for example, without limitation, the UPF2 gene) as the case may be.

In one embodiment, a genetically modified *Cannabis* plant of the disclosure comprises, stably integrated into its genome a nucleic acid molecule heterologous to the plant. The nucleic acid molecule encodes an RNA, e.g. a hairpin RNA, for reducing expression of one or more of the 1,172 genes within the about 20 megabase region (for example, without limitation, the UPF2 gene). The nucleic acid molecule may be arranged in the sense orientation relative to a promoter. In another embodiment, the nucleic acid molecule may be arranged in the anti-sense orientation relative to a promoter. In a further embodiment, a genetic construct may comprise at least two nucleic acid molecules in both the sense and anti-sense orientations, relative to a promoter. A genetic construct comprising nucleic acids in both the sense and anti-sense orientations may result in mRNA transcripts capable of forming stem-loop (hairpin) structures.

In various instances, the nucleic acid molecule comprises at least 20, at least 50, at least 100, at least 150, at least 200, at least 250, at least 300, at least 350, at least 400, at least 450 or at least 500 contiguous nucleotides of a nucleic acid sequence possessing at least 80%, at least 90% or 100% sequence identity to the nucleic acid sequence set forth in SEQ ID NO: 1, The skilled person will also readily understand that although in the foregoing illustrative examples partial gene sequences (e.g. partial UPF2 gene sequences) were suggested for constructing the constructs, complete coding sequences, alternative coding sequences, 5'UTR and/or 3'UTR, or mutated derivatives of these sequences can also be used. The maximum number of nucleic acid molecules that may be used in the context of the invention may be limited only by the maximum size of the construct that may be delivered to a target plant or plant cell using a given transformation method.

The skilled person would also appreciate that a nucleic acid molecule comprising the sequence of a gene promoter and/or other regulatory elements may be used in the context of the invention. For example, a nucleic acid molecular comprising the sequence of a UPF2 gene promoter and/or other regulatory elements may be used in the context of the invention. In an embodiment, a heterologous nucleic acid molecule comprising sequences of a UPF2 gene promoter and/or regulatory element may be used to bias the cellular machinery away from an endogenous UFP2 gene promoter thus resulting in reduced UPF2 expression.

Plant Transformation

The introduction of DNA into plant cells by *Agrobacterium* mediated transfer is well known to those skilled in the art. Use of *Agrobacterium* transformation to transform *Cannabis* plants has been described, for example, in US patent application publication no. 2019/0085347A1.

Nevertheless, the present invention is not limited to any method for transforming plant cells, and the skilled person will readily understand that any other suitable method of DNA transfer into plant cells may be used. Methods for introducing nucleic acids into cells (also referred to herein as "transformation") are known in the art as described in WO2018/027324.

Another method for introducing DNA into plant cells is by biolistics, which involves the bombardment of plant cells with microscopic particles (such as gold or tungsten particles) coated with DNA. The particles are rapidly accelerated, typically by gas or electrical discharge, through the cell wall and membranes, whereby the DNA is released into the cell and incorporated into the genome of the cell. This method is used for transformation of many crops, including corn, wheat, barley, rice, woody tree species and others.

Another method for introducing DNA into plant cells is by electroporation. This method involves a pulse of high voltage applied to protoplasts/cells/tissues resulting in transient pores in the plasma membrane which facilitates the uptake of foreign DNA.

Plant cells may also be transformed by liposome mediated gene transfer.

The nucleic acid constructs of the present invention may be introduced into plant protoplasts, which are cells in which its cell wall is completely or partially removed and then transformed with known methods.

A nucleic acid molecule of the present invention may also be targeted into the genome of a plant cell by a number of methods including, but not limited to, targeting recombination, homologous recombination and site-specific recombination. Methods of homologous recombination and gene targeting in plants are known in the art.

As used herein, "targeted recombination" refers to integration of a nucleic acid construct into a site on the genome, where the integration is facilitated by a construct comprising sequences corresponding to the site of integration.

Homologous recombination relies on sequence identity between a piece of DNA that is introduced into a cell and the cell's genome. Homologous recombination is an extremely rare event in higher eukaryotes. However, the frequency of homologous recombination may be increased with strategies involving the introduction of DNA double-strand breaks, triplex forming oligonucleotides or adeno-associated virus.

"Site-specific recombination" as used herein refers to the enzymatic recombination that occurs when at least two discrete DNA sequences interact to combine into a single nucleic acid sequence in the presence of an enzyme. Enzymes and systems that have been developed to induce targeted mutagenesis and targeted deletions include Zinc Finger Nucleases (ZFNs), Meganucleases, Transcription Activator-Like Effector Nucleases (TALENS), and Clustered Regularly Interspaced Short Palindromic Repeats (CRISPR)-associated nucleases (e.g. CRISPR/Cas9, In one embodiment, the polynucleotide encodes a zinc finger protein that binds to one or more of the 1,172 genes within the about 20 megabase region (e.g. the UPF2 gene), resulting in reduced expression of the gene. In particular embodiments, the zinc finger protein binds to a regulatory region of the gene (e.g. a regulatory region of the UPF2 gene). In other embodiments, the zinc finger protein binds to mRNA (e.g. UPF2 mRNA) to prevent its translation. Methods of selecting sites for targeting by zinc finger proteins have been described, for example, in U.S. Pat. No. 6,453,242, and methods for using zinc finger proteins to inhibit the expression of genes in plants are described, for example, in US2003/0037355.

The nucleic acid molecule becomes stably integrated into the plant genome such that it is heritable to daughter cells in order that successive generations of plant cells have reduced gene expression. This may involve the nucleic acid molecules of the present invention integrating, for instance randomly, into the plant cell genome. Alternatively, the nucleic acid molecules of the present invention may remain as exogenous, self-replicating DNA that is heritable to daughter cells. As used herein, heterologous, self-replicating DNA that is heritable to daughter cells is also considered to be "stably integrated into the plant genome".

Disruption of an endogenous gene (for example, without limitation, the endogenous UPF2 gene) may be confirmed by methods known in the art of molecular biology. For example, disruption of endogenous genes may be assessed by PCR followed by Southern blot analysis. mRNA levels may, for example, be measured by real time PCR, RT-PCR, Northern blot analysis, micro-array gene analysis, and RNAse protection.

Targeted Screening for Loss or Gain of Function Gene Mutations

This disclosure further relates to methods of generating Cannabis plants with day length neutral phenotype that involve targeted screening for loss or gain of function mutations in one or more of the 1,172 genes within the about 20 megabase region (for example, without limitation, the endogenous UPF2 gene) and subsequent breeding of plants to obtain plants homozygous for the loss or gain of function mutation at the locus. Cannabis breeders have used a variety of selection techniques in the development of improved cultivars. However, the most successful breeding method involves the hybridization of parents with a variety of different desired characteristics.

The term "T-DNA insertion" refers to methods utilizing transfer-DNA (T-DNA) for disrupting genes via insertional mutagenesis. Down-regulating or silencing expression of the endogenous gene (for example, without limitation, the endogenous UPF2 gene) could be achieved by T-DNA mutagenesis, wherein the T-DNA is randomly inserted in the plant genome to introduce mutations. Subsequently, plants can be screened for T-DNA insertions in the gene.

Mutations (including deletions, insertions, and point mutations) can also be introduced randomly into the genome of a plant cell by various forms of mutagenesis to produce non-natural variants. Methods for mutagenesis of plant material, including seeds, and subsequent screening or selection for desired phenotypes are well known, as described in WO2009/109012. Mutagenized plants and plant cells can also be specifically screened for mutations in any one of the 1,172 genes within the about 20 megabase region (for example, without limitation, the UPF2 gene), for example, by TILLING (Targeting Induced Local Genomes). Loss or gain of function mutations present in natural plant populations can be identified by EcoTILLING.

Once the loss or gain of function mutation in the endogenous gene has been identified, traditional breeding processes can be used to produce plants homozygous for the loss or gain of function mutations at the endogenous gene.

Plants Having an Autoflowering ("Day Length Neutral") Phenotype

The skilled person further understands that aspects of this disclosure pertain to novel plants having a day length neutral phenotype, or that are carriers of the day length neutral phenotype.

In one aspect, the disclosure pertains to a Cannabis plant or plant cell generated according to a method as described above in the section entitled "Marker-assisted Breeding" and "Molecular Modification".

In another aspect, the disclosure pertains to a genetically modified Cannabis plant or plant cell having a photoperiod phenotype, wherein the Cannabis plant or plant cell is genetically modified to have reduced expression of one or more of the 1,172 endogenous genes within the about 20 megabase region (for example, without limitation, reduced expression of the endogenous UPF2 gene). In various embodiments, the plant or plant cell comprises an expression construct for reducing the expression of the endogenous gene (for example, without limitation, the endogenous UPF2 gene). The expression construct comprises a nucleic acid molecule encoding a hairpin RNA for reducing expression of the endogenous gene (for example, without limitation, the endogenous UPF2 gene). For example, the endogenous UPF2 gene may have the sequence of SEQ ID NO: 1 or be at least 95% identical to SEQ ID NO: 1. The nucleic acid molecule encoding the hairpin RNA may comprises a portion of SEQ ID NO: 1. In some embodiments, the plant or plant cell is a seed or seed cell.

In various aspects, the disclosure pertains to seeds produced by a Cannabis plant or plant cell as described above. In various aspects, the disclosure pertains to a method of producing seeds comprising growing a Cannabis plant as described above, allowing the Cannabis plant to flower, be pollinated, and set seed, and harvesting the seed from the plant.

In various aspects, the disclosure pertains to dried flower from a Cannabis plant having a day length neutral phenotype as described above, or comprising a Cannabis plant cell as described above.

In various aspects, the disclosure relates to a crop comprising a plurality of Cannabis plants as described above.

In various aspects, the disclosure relates to expression vectors for generating a day length neutral Cannabis plant, the expression vector comprising a nucleic acid comprising a portion of SEQ ID NO. 1.

In various aspects, the disclosure relates to use of a polynucleotide molecule having a sequence comprising a portion of SEQ ID NO: 1 for generating a Cannabis plant with a day length neutral phenotype.

In various aspects, the disclosure relates to use of a plant or plant cell as described above for the production of cannabinoids and/or terpenes.

Value Added Products

The skilled person understands that the disclosure further pertains to cannabinoids and/or terpenes derived from a plant or plant cell as described above, or extracted from dried flower as described above. Thus, the disclosure further pertains to methods of producing cannabinoids and/or terpenes comprising extracting cannabinoids and/or terpenes from flowers harvested from plants as described above.

The skilled person further understands that the plants and plant cells described above could further be used to derive extracts, concentrates, isolates, and oils containing cannabinoids and/or terpenes, which may be consumed or optionally used in the production of a variety of food items. The food items may be edible oils. The food items may be snack foods, e.g. candy. The candy may be chocolate, gummies, mints, lozenges, lollipops, or chewing gums. The food items may be baked goods, including, but not limited to, cookies, brownies, cakes, or breads. The food items may be beverages including, but not limited to, soft drinks, energy drinks, teas, coffees, juices, or waters.

The skilled person further understands that the plants and plant cells described above could further be used to derive extracts, concentrates, isolates, and oils containing cannabinoids and/or terpenes, which may be used in the production of cosmetics and/or topicals. The topicals may be massage creams, massage oils, bath oils, body oils, cosmetic oils, oils for toiletry purposes, skin creams, skin lotions, lip care preparations, face and body lotions, bath additives, soaps for personal use, beauty creams for body care, non-medicated skin preparations, or medicated skin preparations.

The disclosure further pertains to extracts, concentrates, isolates, and oils containing cannabinoids and/or terpenes derived from a *Cannabis* plant or plant cell, or dried flower, as described above, and pharmaceutical compositions comprising such extracts, concentrates, isolates, and oils, wherein the extracts, concentrates, isolates, and oils contain cannabinoids and/or terpenes.

The disclosure further pertains to methods of producing oils containing cannabinoids and/or terpenes, the methods comprising crushing seeds produced by a plant described above.

The disclosure further pertains to methods of producing oils, extracts, and concentrates containing cannabinoids and/or terpenes, the methods comprising extracting the oils, extracts, and concentrates from a plant or plant cell, or dried flower, as described above.

The disclosure further pertains to methods of producing isolates comprising a cannabinoid or terpene, the methods comprising isolating the cannabinoid or terpene from a plant or plant cell, or dried flower, as described above.

While specific embodiments of the invention have been described and illustrated, such embodiments should be considered illustrative of the invention only and not as limiting the invention as construed in accordance with the accompanying claims.

All applications and publications referred to herein are incorporated by reference in their entirety.

TABLE 1

Polymorphic sites located within a 20 megabase region of the Cannabis chromosome CM010796.2 located between about 40 megabases to about 60 megabases.

| Polymorphism ID | Chromosome | Haplotype | Variant | Genomic Context Sequence | SEQ ID NO: |
|---|---|---|---|---|---|
| SCM010796.2_55541136 | CM010796.2 | GGAAAAGGAA (SEQ ID NO: 47)/ GAGAAAAGAA (SEQ ID NO: 48) | GAGAA AAGAA (SEQ ID No: 48) | GCTACTGGAAACCTGTCTATTTTCTAGTGCAATGAAGTATAATAT GGACAATGAGGCAAGGCAATGTAAGTAGGTTAAGAGATAAAAG TTTCAAGGCACTGGAAAAGGAATTGGAAAGTATAATCATAGTTA GGCAGAGAAAGATTTGAACTGTTATACGGTTCTTTTATGGGATG GGAGTTTATTATGAATTTCAAGTGGAGAAAAAAAA | 5 |
| SCM010796.2_56140841 | CM010796.2 | G/T | T | AACACTCAACACACAAATATACAAATATCAAATACACATACACTC ACACACACAAATGGTAATGAAAGAAAGAAGACGGTACCTTAAAA GCAGAACGAGCGACATAGCCCAGGCGTTGAGCTTCTCTGTAGAA AAAATCTGGAGCTCCAGCTCCACTCATCTCTGCAAATGTTAAAAC CCTAAACCCCGGTAGTCGCACAG | 6 |
| SCM010796.2_57309299 | CM010796.2 | T/A | A | CTGGCGGTGCCCAAAATTTTGGGCACCCGGTTGAAAATTTGATTG CCTGGTTGGGAACTTTTTCGAGTATCTCAATTTTTGTGATATTTAG GATATTGACTCTTCATTTATGGATGGAAAAATTTTAAATTATAAAT TTAAGTTGTAAAAAGTATTTTAGTGAGACATATACCAATTTACCA TTAAATATTTTCTACTACT | 7 |
| SCM010796.2_50858909 | CM010796.2 | G/A | A | GTTATATGGAGACTTCACATCCACCACTAACAACGTGGCCATGAT GGTGGTTTACCTTGGGCTAGTGCTGCTAGTGAGTGGCAGTTTGA TCTTGCCACATGGAGTAATGGCAGCTCCACTGAAACCATACATTA GATGTTCGCATGGATTTAGGTGTTTGAGTGACAAACCAATCTGG ATTAAAGTTTGCTTGAATAAGAT | 8 |
| SCM010796.2_44181271 | CM010796.2 | A/G | G | CCTCCTTGTTTTTACATAATCAATGCATGCCTTATTCTTCTTTTACT TTATCTTTATTTTTTTTTCTTTAAAATTACATTTTCTTTAGTTTATT GGTGATATCCCTTCTAGCTTAGCATAATTTTGCCTGTACTATTAAGG CAATCAAATTTTGTCTTCATTTTTACAATTTTAGTATTTTCTTGTAC TGAATAAGATTTT | 9 |
| SCM010796.2_40320374 | CM010796.2 | C/T | T | GTGTCTCCCTAAATCCCGTGGGAGCCTTGGCTTCCGAAAAACTAA GAAAATGAATCAGGATTTCTTGGCTAAGTAGGCTTGGAAACTGC TTACTAAATCCCAATCTTTGTGTTGAAGAATTCTAAGAGCTAAAT ACCTTAGAGGAAAGGATATGCTTAAGTGTAAGGCTAAGTCTGTT GACTTTTGGTTTTAGAAAAGTGT | 10 |

TABLE 1-continued

Polymorphic sites located within a 20 megabase region of the Cannabis chromosome CM010796.2 located between about 40 megabases to about 60 megabases.

| Polymorphism ID | Chromosome | Haplotype | Variant | Genomic Context Sequence | SEQ ID NO: |
|---|---|---|---|---|---|
| SCM010796.2_59999985 | CM010796.2 | A/G | G | CCTTCAGATTATAATACAAAACACAATAAGAAATTTGAAAATACA GATAAAGAAGCAATATATAACCATGTGGAACTGTTCAAGTATGTC TACGCAATCAACATTACCGGATTTCCATCAGAATCTCCAAAGCCT TTTTTGGGACCATATTAATAGATTGCAACTGAAAATTTCCATGTCA ACATTAGTAGAAGAAGATCA | 11 |
| SCM010796.2_54639687 | CM010796.2 | G/A | A | TTTAAATGAGTAATTTAATTTCATGTTATTATACGTAAAAAAAAT ATATGTATATATATGAAAATTAACATTAAAATTTTACTTTTTATTTT TGGATTAGATTTATCCAATTCAATCCAATAATAATACTAGATCTAAAT TATTGGATGAATCTAATTCGATCCATAAATATTAGGTGTAAAATA TTAGATAAACTTGAATT | 12 |
| SCM010796.2_51022534 | CM010796.2 | T/C | C | ACTGGTTTAATATATAAATATATAAAATAATATAAAATTTAAAAG AAGAAGAATATAAAGAGAGAAAAAAATTAAATGAAAATTTTTCA GTTAGAGTGAATTCTTATTTATACAAAAATATGATTAAAAGAATG AAAAATTAAACTAATGTAATAAAGAAAAATACAACTAAGCATTAA TGGCGATAATTAATTTGGTGAT | 13 |
| SCM010796.2_48159974 | CM010796.2 | A/T | T | CTAAGTTTGAGATGAAGGACTTAGGAAATGCCACTTAAATCCTTG GAATAATTATTGTGAGGGATAAAGGCAAGGGATCCTAAAGATGT GTCAGGAAGATAACATTCAGAAGGTGATTGAGAAGTGTTGGGA ATATTTTACTAGGATCTAGATTTACTAACAAGTATGATGATTAAC ATCCTAAATATGAATATCTCTAAA | 14 |

TABLE 2

Polymorphic sites located within +/-10 kb region of the Cannabis UPF2 gene.

| Polymorphism ID | Chromosome | Haplotype | Variant | Genomic Context Sequence | SEQ ID NO: |
|---|---|---|---|---|---|
| SCM010796.2_0 | CM010796.2 | AATGTGTTGTA ATGGTACTCAT CGTTTTAGTTG CCCCACGGCT ACAAATGTTTT CAAATCGTTTC GAGTCCAATT GGGTAAGGTG TGGTAATTAA AACAAATCTAT AATGATAATG TAATACCAACC TTATACGACCA ATTCTTGTATG GTATCCATATT GTTTTGGACA GTT (SEQ ID NO: 49)/ AATGTGTTGTA ATGGTACTCAT CGTTTTAGTTG CCCCACGGCT ACAAATGTTTT CAAATCGTTCG AGTTCCAATTG GGTAAGGTGT GGTAATTAAA ACAAATCTATA ATGATAATGT AATACCAACCT ATACGACCAA TTCTTGTATGG TATCCATATTG TTTTGACAGTT (SEQ ID NO: 50) | AATGTGTTGTAA TGGTACTCATCG TTTTAGTTGCCC CACGGCTACAA ATGTTTTCAAAT CGTTCGAGTTCC AATTGGGTAAG GTGTGGTAATTA AACAAATCTAT AATGATAATGTA ATACCAACCTAT ACGACCAATTCT TGTATGGTATCC ATATTGTTTTGA CAGTT (SEQ ID NO: 50) | AATATGCATTTAGAATGGTTGAG AGTTTATGATAATGATAATGCAA TACCAATTTCATATGACCAATTC CTCTATTGTATCCATATTGTTTT GGACAGTTAATGTGTTGTAATGG TACTCATCGTTTTAGTTGCCCCA CGGCTACAAATGTTTTCAAATCG TTTCGAGTCCAATTGGGTAAGGT GTGGTAATTAAAACAAATCTATA ATGATAATGTAATACCAACCTTA TACGACCAATTCTTGTATGGTAT CCATATTGTTTTGGACAGTTGTT TTTTTTTTTCTTGTAATGGTAC TCACCGTTTCAGTTGTCCAATGT TTTCAAATCGTGTTTTGAGTCCA ATTGGAAAAGGTGTGGT | 15 |

TABLE 2-continued

Polymorphic sites located within +/-10 kb region of the Cannabis UPF2 gene.

| Polymorphism ID | Chromosome | Haplotype | Variant | Genomic Context Sequence | SEQ ID NO: |
|---|---|---|---|---|---|
| SCM010796.2_1 | CM010796.2 | AGTCC/AGTCA | AGTCA | ATTGATTATAAAATAAATAGAGCTTAAGAAACAAAAAAATTAAGAAGAAGAAAACTAAGATTTTTACGTGGTTGGAGCGTTGATGAACTTTAGTCCACGAGTCCATATATTATTAATTTGAGAAACTTGATGTTTTACACAAGGATAATATTTTTTCCAAACTTAAGAACCCTAATTTAAGTCTTAGTATTTGAATAAT | 16 |
| SCM010796.2_2 | CM010796.2 | ATTAA/ATAA/GTTAG/ATTAG | ATAA/GTTAG/ATTAG | ATAAATAGAGCTTAAGAAACAAAAAAATTAAGAAGAAGAAAACTAAGATTTTTACGTGGTTGGAGCGTTGATGAACTTTAGTCCACGAGTCCATATATTATTAATTTGAGAAACTTTGATGTTTTACACAAGGATAATATTTTTTCCAAACTTAAGAACCCTAATTTAAGTCTTAGTATTTGAATAATGATTTTCCACCA | 17 |
| SCM010796.2_3 | CM010796.2 | T/C | C | AAAATTAAGAAGAAGAAAACTAAGATTTTTACGTGGTTGGAGCGTTGATGAACTTTAGTCCACGAGTCCATATATTATTAATTTGAGAAACTTTGATGTTTTACACAAGGATAATATTTTTTCCAAACTTAAGAACCCTAATTTAAGTCTTAGTATTTGAATAATGATTTTCCACCATTTGCATGAAGATACAATCTTCTAAGA | 18 |
| SCM010796.2_4 | CM010796.2 | T/G | G | TTTTTACGTGGTTGGAGCGTTGATGAACTTTAGTCCACGAGTCCATATATTATTAATTTGAGAAACTTTGATGTTTTACACAAGGATAATATTTTTTCCAAACTTAAGAACCCTAATTTAAGTCTTAGTATTTGAATAATGATTTTCCACCATTTGCATGAAGATACAATCTTCTATTATAGGCTAGGGTTAAGACA | 19 |
| SCM010796.2_5 | CM010796.2 | A/G | G | GGTTGGAGCGTTGATGAACTTTAGTCCACGAGTCCATATATTATTAATTTGAGAAACTTTGATGTTTTACACAAGGATAATATTTTTTCCAAACTTAAGAACCCTAATTTAAGTCTTAGTATTTGAATAATGATTTTCCACCATTTGCATGAAGATACAATCTTCTATTATAGGCTAGGGTTAAGACAGTTAGGATTTTTG | 20 |
| SCM010796.2_6 | CM010796.2 | T/A | A | GTTTTACACAAGGATAATATTTTTTCCAAACTTAAGAACCCTAATTTAAGTCTTAGTATTTGAATAATGATTTTCCACCATTTGCATGAAGATACAATCTTCTATTATAGGCTAGGGTTAAGACAGTTAGGATTTTTGTATGAAGCTAAACCCACTGAAGGAGTAAATACATTTAATAGTGACTTTAGATTAATTAGAAAA | 21 |
| SCM010796.2_7 | CM010796.2 | ATTATAGGCTAGG (SEQ ID NO: 51)/ATTTATAGGCTAGG (SEQ ID NO: 52)/ATTTAGCCGCTAA (SEQ ID NO: 53)/ATTTATACGCTAGG (SEQ ID NO: 54) | ATTTATAGGCTAGG (SEQ ID NO: 52)/ATTTAGCCGCTAA (SEQ ID NO:53)/ATTTATACGCTAGG (SEQ ID NO: 54) | TTACACAAGGATAATATTTTTCCAAACTTAAGAACCCTAATTTAAGTCTTAGTATTTGAATAATGATTTTCCACCATTTGCATGAAGATACAATCTTCTATTATAGGCTAGGGTTAAGACAGTTAGGATTTTTGTATGAAGCTAAACCCACTGAAGGAGTAAATACATTTAATAGTGACTTTAGATTAATTAGAAAAGAA | 22 |

TABLE 2-continued

Polymorphic sites located within +/-10 kb region of the Cannabis UPF2 gene.

| Polymorphism ID | Chromosome | Haplotype | Variant | Genomic Context Sequence | SEQ ID NO: |
|---|---|---|---|---|---|
| SCM010796.2_8 | CM010796.2 | G/T | T | ACTTAAGAACCCTAATTTAAGTC TTAGTATTTGAATAATGATTTTC CACCATTTGCATGAAGATACAAT CTTCTATTATAGGCTAGGGTTAA GACAGTTAGGATTTTTGTATG AAGCTAAACCCACTGAAGGAGTA AATACATTTAATAGTGACTTTAG ATTAATTAGAAAAGAACTCATTT ACAAGATAACGATCATCTA | 23 |
| SCM010796.2_9 | CM010796.2 | G/A | A | CTTAAGAACCCTAATTTAAGTCT TAGTATTTGAATAATGATTTTCC ACCATTTGCATGAAGATACAATC TTCTATTATAGGCTAGGGTTAAG ACAGTTAGGATTTTTGTATGA AGCTAAACCCACTGAAGGAGTAA ATACATTTAATAGTGACTTTAGA TTAATTAGAAAAGAACTCATTTA CAAGATAACGATCATCTAT | 24 |

TABLE 3

Polymorphisms Somewhat Associated with Autoflowering Phenotype in Cannabis, Located within +/-500 kb of UPF2 gene

| Polymorphism ID | Chromosome | Haplotype | Predictive Variant of Autoflowering | Genomic Context Sequence | SEQ ID NO: |
|---|---|---|---|---|---|
| SCM010796.2_1001 | CM010796.2 | C/G | G | CATttggttattatatatatatt catgatttttttttttctattta ttactATTGACAATGttgttatt ttagttatttcaaactttttaatt gcattacaCttgtaaggataa tattttatggagtattaaatat aaataaagagtgatatttaattt ttatgtattttcttcatatttg gaaattaatactaaaaatt | 25 |
| SCM010796.2_1002 | CM010796.2 | T/C | C | ACTTGTTATAAATTATAGTTGAA CTTCTTTATATTGTTATTGCTCA AATAGAAGTTAACAATTATACAA GTCTTATACATTATGGGTTCAGA AACTTTGATTGAAGTGATATT GGCTATACTCCTTCCTCCAGTGG GTGTTTTCCTCCGCTTTGGTTGT GCGGtaataattaatcttaaata tCTTATTATGTCTATGCCA | 26 |
| SCM010796.2_1003 | CM010796.2 | G/T | T | CAAGGTCTGCTCAATTCCTTGAT CATCAAGCAATCTCAATTCCTTG ATCATCAAGCAATTTATCAGTAG TGTTGTTAGTGGGTTTGCTATTA GctttttGtaaaaaaaaaa aaaaaaaaaaaaaaaaacgagtg TTCGAGTCTCCTAATTTGAGCCA AAAAACACGAGACCGTTGTTGGC AATAATCCTCTTCTTAAGC | 27 |
| SCM010796.2_1004 | CM010796.2 | C/T | T | aagaaggagggtttcggcatcaaa gattcagagaaagagatccaggt tcagatattgataatgctctgct acagaaaggaatcaagggctaga tatctgaaCggaaggagtcat tatattccgctgcaaccaatgta aggtttcctaaactttatatgtg tttatttcatcgttttagaaagt tcatatttagggtgttaat | 28 |

TABLE 3-continued

Polymorphisms Somewhat Associated with Autoflowering Phenotype in Cannabis, Located within +/-500 kb of UPF2 gene

| Polymorphism ID | Chromosome | Haplotype | Predictive Variant of Autoflowering | Genomic Context Sequence | SEQ ID NO: |
|---|---|---|---|---|---|
| SCM010796.2_1005 | CM010796.2 | TAT/TT | TT | TTTTTCTCCCATCTGATTCAAAT GTAATATTTTGATTGAAATTCAC TCAAATAAGAGGAAGACAGAGAA GGAGTGAAAAGACCAAGATTGGC AGAGTTATTAT ACCAAACAAGAAAAGAGCAAAAT ACTAACATGTAAGGATATTAAGA CAAAGACAATTTAGTGATGAAAC TTACAGAAGCTCTGAACTTATCA ATCTCT | 29 |
| SCM010796.2_1006 | CM010796.2 | T/C | C | TTGACACAACACGAAACTGGCAC GAGCACAATTAGACACGAAAAA ATATGGGCATTAGCACGACATA GGCACGACAAAAGATGAAAAAT ATGTCCTTAAGTACAATACG ACACGAGAAGTAGGGCTGAACA TTTAAACCCGCAAACCCGAAAA CCCGGCAACCCACCCCGACCCG CTGCCGAAAAAAAACCGAAAAA TTGA | 30 |
| SCM010796.2_1007 | CM010796.2 | G/A | A | ACCTTTGAAAGGGATCCTTTCA TTTTGAACATGAACTTATTGTC TCTTATACCGTCaagaatttaa ttaattctCCATAATAAAAAAG TATTGAATGAGTGGTTTGGT GGTAAAATGCTTACTCTCAACT AGTTTTTTAAGCcgttaaatat aagaaaaatgtcTCGCAGCTTA GCCACCCTAGACATCCATTTTA GGCAC | 31 |
| SCM010796.2_1008 | CM010796.2 | T/A | T | Tttgattgtttttttaaaataa gataaaaagataaaatagaaat atttatgaaaataaagaattat ataAGTGAAAATGTTTTAGACA AaacgtTaaaaataaaaaaa aaaaaaaaaaaaaaaaaaaaaa aaaaaggagtacAACGGTTTAT GCAAACGtgtataattaaccta ataattataataagaatAGAAT TAGGa | 32 |
| SCM010796.2_1009 | CM010796.2 | T/G | G | AAGAAGTTGAACCTCCTCATGA GACAAAGACAAATAGTAGTTCT TTGACTGATCTTCAAAGAAGCA TTATAAAAGAATTATTAGAAAT CATATCGTCTCCTATTGAAA ATAAACAACAACAAGATCAATC TAATGAAgttgataaaataatt attcaagaTGATGGCATAGGCC TCGATGATCTCCCTGAGGAATT CTTCA | 33 |
| SCM010796.2_1010 | CM010796.2 | A/C | C | atttttatgaatcttAAATTC AAAttctttttttaatgttta tatggtttttttttttttttta gtttaattggttaaataatgtc atatttagtggcAtttactt tttatgtcatatttatcataac cttaataattttttccatattt tttaaaatagccCATCAAATTT TGTCCCCGAATGTTAAGCGGGG CGGGA | 34 |

TABLE 4

Polymorphisms Significantly Associated with Autoflowering
Phenotype, Located on Chromosome CM010796.2

| Polymorphism ID | Chromosome | Haplotype | Predictive Variant of Autoflowering | Genomic Sequence Context | SEQ ID NO: |
|---|---|---|---|---|---|
| SCM010796.2_2001 | CM010796.2 | G/A | A | aataataaataaaaactttaaca aaaaaaattaattaaaaaattat tcgaactttaaattaatttaat aaactaACCAATTTCATGAGTTA CTAATaatGttttattaattt atatttaaaagttaatctTGTAT CTTTGCTAAACTTGTATTATAGA GCAATTTTaatagattttaaaa ttatttataaaagtattaa | 35 |
| SCM010796.2_2002 | CM010796.2 | T/C | C | aaataattattatttagttttGA TAATAAAGTTATTGGTaagattt catatatatacatattattaata acttttatatttgattataatt tattaattTcttaaatattaa ttaacatgaaaaaattactaaat aaagTAACATAAATATATCTTAA ATTAGCAATCAATTTCATGGGtt acttaaaattattttatt | 36 |
| SCM010796.2_2003 | CM010796.2 | A/T | T | taattaaatttcttaatttgTAA CTAATCTATAAGAagtcatgaaa agaaaaaatattttaagaaaatt ggTAAGCAAATTTATAattcata taataataAtagattgATGTAAA TTATAGAGAAAAGTAAAACTCAA TACCAAATTACAATAAATCTTAA ATTATAAATGTTAGATCGTAAGT agaccaaacaaaaaaaa | 37 |
| SCM010796.2_2004 | CM010796.2 | C/T | T | acataaattaattaataactata TACTGATTGAATAAAGAGGATAA GAAAAAACTTATCACATCAAAAT GATCTCCAAatcttcattatttt taaatatcCcATTTGTTTCGAAC ATTGTTATATATCTACTTTGTTC CACCTACACCACTTAGACGAAAC CCAATGCAGTTTGCTAACGTTAA AGATTAGCCAATTTAGT | 38 |
| SCM010796.2_2005 | CM010796.2 | T/A | A | TGATTGAATAAAGAGGATAAGAA AAAACTTATCACATCAAAATGAT CTCCAAatcttcattattttaa atatcccATTTGTTTCGAACATT GTTATATATCTACTTTGTTCC ACCTACACCACTTAGACGAAACC CAATGCAGTTTGCTAACGTTAAA GATTAGCCAATTTAGTTTACATT TTCATTACATTTTGCTCTA | 39 |
| SCM010796.2_2006 | CM010796.2 | A/G | G | TGATTATTCGGATTGAAACAata gataatttatagcgtatctattc TTGGTGAATAGAGTATTTTATGT AATCAGGAGTGCAATTTCGAATC TATAGTTGAGTGAGGAggaatta ataataaagaaaatttacttgat aaattctaGAATTACTTATTGAg tgcttgattatataggcccatgt ccttgtactagttgaga | 40 |
| SCM010796.2_2007 | CM010796.2 | G/A | A | ggaattaataataaagaaaattt acttgataaattctaGAATTACT TATTGAgtgcttgattatatagg cccatgtccttgtactagttgag ataataatGtcttgtagactc aattaattaattttaattaatca attagaattctaTTTATGagttt cactaagtaagggcttatttgag aagaaaatgaggatttaag | 41 |
| SCM010796.2_2008 | CM010796.2 | T/C | C | AAGGTACAATCTATGctactata ttttaaaatattcattATACATT GTAAATATTGaaatatgtaaatt | 42 |

TABLE 4-continued

Polymorphisms Significantly Associated with Autoflowering
Phenotype, Located on Chromosome CM010796.2

| Polymorphism ID | Chromosome | Haplotype | Predictive Variant of Autoflowering | Genomic Sequence Context | SEQ ID NO: |
|---|---|---|---|---|---|
| | | | | ttttacTTATATTTCAGGTTGAa agtatataTgtttatatatgcaC ACACGTCTATAATGAAAggtttt tgttttaatttcaatttcaagaa taaaaattacagtaatttaaatt gaattcatatctttctt | |
| SCM010796.2_ 2009 | CM010796.2 | T/C | C | ATCTATGctactatattttaaaa tattcattATACATTGTAAATAT TGaaatatgtaaattttttacTT ATATTTCAGGTTGAaagtatata tgtttataTatgcaCACACGT CTATAATGAAAggttttgtttt aatttcaatttcaagaataaaaa ttacagtaatttaaattgaattc atatctttcttttAATTAC | 43 |
| SCM010796.2_ 2010 | CM010796.2 | C/T | T | catattttaatagtggtatatat aattttgttagcatgatatatat tttttgagtattaatttagtatt gttataattttttgtggtatat aattttatCactatagtatat taattttcagtaATACGATATAT CAAATACTGctgtatatatttaa tgatctaatattttattcatttt gttacaatataataatatg | 44 |

What is claimed is:

1. A method for producing a *Cannabis* plant having a day length neutral phenotype, or carrying a trait for a day length neutral phenotype, the method comprising:
   producing a *Cannabis* plant having a day length neutral phenotype, comprising:
   first, performing a cross of a first parent having at least one allele associated with a day length neutral phenotype, with a second parent that has a day length sensitive phenotype, to produce a first progeny plant,
   second, identifying a first progeny plant from the first cross that has the day length neutral phenotype, or that is a carrier of a trait for the day length neutral phenotype,
   third, performing a cross of a first progeny plant that has the day length neutral phenotype, or that is a carrier of a trait for the day length neutral phenotype, with a second first progeny plant that has the day length neutral phenotype, or that is a carrier of a trait for the day length neutral phenotype, to produce a second progeny plant, and
   identifying a *Cannabis* plant having a day length neutral phenotype or carrying a trait for a day length neutral phenotype, comprising testing nucleic acid from the *Cannabis* plant to determine the presence or absence of an allele,
   wherein the allele is in linkage disequilibrium $r^2=0.9$ to 1 with a variation in a polymorphic site in the endogenous UPF2 gene
   wherein the variation in a polymorphic site in the endogenous UPF2 gene corresponds to a polynucleotide with a sequence as set forth in SEQ ID NO: 2, and wherein the absence of SEQ ID NO: 2 or a portion thereof from the endogenous UPF2 gene is associated with the day length neutral phenotype, and
   wherein the presence of the allele indicates that the plant has a day length neutral phenotype or is a carrier of the trait for the day length neutral phenotype.

2. The method of claim 1, wherein the testing nucleic acid from the *Cannabis* plant comprises nucleic acid amplification.

3. The method of claim 2, wherein the nucleic acid amplification is carried out by polymerase chain reaction.

4. The method of claim 1, wherein the testing nucleic acid from the *Cannabis* plant is performed using an allele-specific method, and wherein the allele-specific method is allele-specific probe hybridization, allele-specific primer extension, or allele-specific amplification.

5. The method of claim 1, wherein the absence of the polynucleotide corresponding to the sequence set forth in SEQ ID NO: 2 or a portion thereof in two copies of the endogenous UPF2 gene indicates that the plant has a day length neutral phenotype, and wherein the absence of the polynucleotide corresponding to the sequence set forth in SEQ ID NO: 2 or a portion thereof from one copy of the UPF2 gene indicates that the plant is a carrier of the trait for the day length neutral phenotype.

6. The method of claim 1, wherein presence of the variation in a polymorphic site in two copies of the chromosome indicates that the plant has a day length neutral phenotype.

7. The method of claim 1, wherein presence of the variation in a polymorphic site in a single copy of the chromosome indicates that the plant is a carrier of the trait for the day length neutral phenotype.

8. The method of claim 1, wherein the variation in a polymorphic site is a loss of function mutation or a gain of function mutation.

9. The method of claim 1, wherein the variation in a polymorphic site is a point mutation, a deletion, or an insertion.

* * * * *